(12) United States Patent
Le et al.

(10) Patent No.: US 8,507,203 B2
(45) Date of Patent: Aug. 13, 2013

(54) **APTAMERS SELECTED AGAINST LIVE *S. PYOGENES* CELLS**

(75) Inventors: X. Chris Le, Edmonton (CA); Camille Hamula, Edmonton (CA); Xing-Fang Li, Calgary (CA)

(73) Assignee: The Governors of the University of Alberta, Calgary, Alberta (CA)

( * ) Notice: Subject to any disclaimer, the term of this patent is extended or adjusted under 35 U.S.C. 154(b) by 0 days.

(21) Appl. No.: 13/433,553

(22) Filed: Mar. 29, 2012

(65) Prior Publication Data

US 2012/0276547 A1 Nov. 1, 2012

Related U.S. Application Data

(60) Provisional application No. 61/468,706, filed on Mar. 29, 2011.

(51) Int. Cl.
| | |
|---|---|
| *C12Q 1/68* | (2006.01) |
| *C07H 21/02* | (2006.01) |
| *C07H 21/04* | (2006.01) |
| *G01N 33/569* | (2006.01) |
| *G01N 33/53* | (2006.01) |

(52) U.S. Cl.
USPC ............. 435/6.1; 536/23.1; 435/7.1; 435/7.2; 435/7.34; 435/7.8

(58) Field of Classification Search
None
See application file for complete search history.

(56) References Cited

U.S. PATENT DOCUMENTS

| | | | | |
|---|---|---|---|---|
| 5,270,163 | A * | 12/1993 | Gold et al. | 435/6.11 |
| 2007/0292397 | A1* | 12/2007 | McNulty et al. | 424/93.6 |
| 2010/0166732 | A1* | 7/2010 | Meinke et al. | 424/130.1 |

OTHER PUBLICATIONS

Vlaminckx et al (Infection and Immunity, May 2007, p. 2603-2611).*

Hamula, Camille L.A. et al.; DNA Aptamers Binding to Multiple Prevalent M-Types of *Streptococcus pyogenes*; American Chemical Society; Anal. Chem. 2011; vol. 83; pp. 3640-3647.

* cited by examiner

*Primary Examiner* — Richard Schnizer
(74) *Attorney, Agent, or Firm* — Bennett Jones LLP

(57) ABSTRACT

The invention is directed to aptamers, methods and kits comprising same for detecting *Streptococcus pyogenes*. The method of screening a subject for *Streptococcus pyogenes* involves obtaining a body sample from the subject; contacting the sample or a bacterial culture of the sample with an aptamer or a panel of aptamers specific to *S. pyogenes*; and detecting the presence or absence of *S. pyogenes* in the sample or the bacterial culture, wherein binding of the aptamer is indicative of the presence of *S. pyogenes*.

17 Claims, 30 Drawing Sheets

20A9P     Kd = 13 ± 1 Nm   SEQ ID NO: 9

20A9    Kd = 9 ± 1 nM    SEQ ID NO: 8

20A24P   Kd = 9 ± 1 nM   SEQ ID NO: 13

20A12P    Kd = 25 ± 3 nM    SEQ ID NO: 10

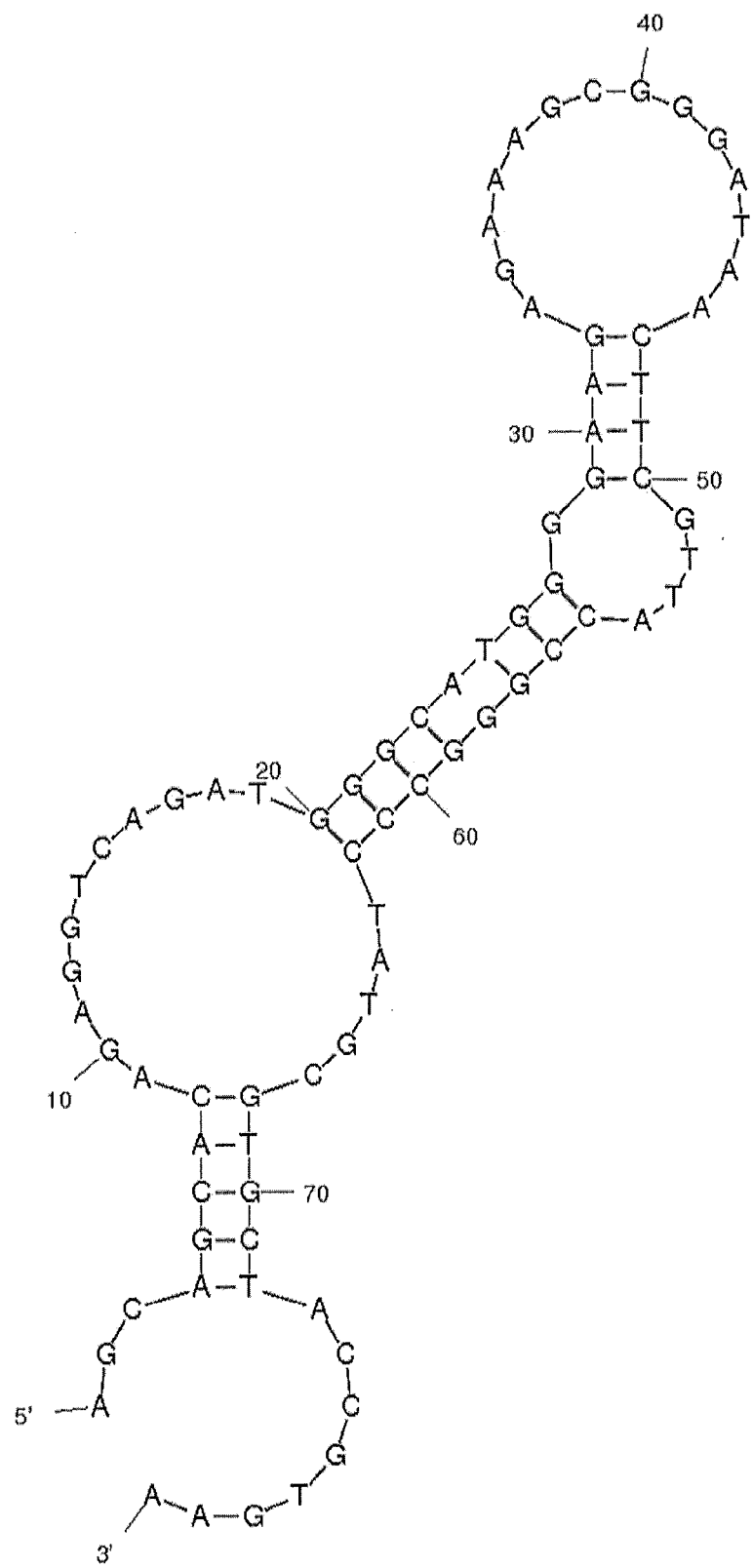
FIG. 10E   20A14P   Kd = 17 ± 1 nM   SEQ ID NO: 11

15A3P   Kd = 10 ± 1 nM   SEQ ID NO: 15

1=neg control PCR; 2=neg So; 3= library So; 4=neg W1; 5=W1; 6=neg W2; 7=W2; 8=neg W3; 9=W3; 10=neg CA; 11=CA fraction; 12=neg cells; 13=cell fraction 1=neg control PCR; 2=neg So 3D; 3= So 3D  4= neg So 3E; 5=So 3E; 6=W1 3D; 7=W1 3E;

E cells 1    SEQ ID NO: 31

E cells 1P   SEQ ID NO: 32

D cells 9   SEQ ID NO: 22

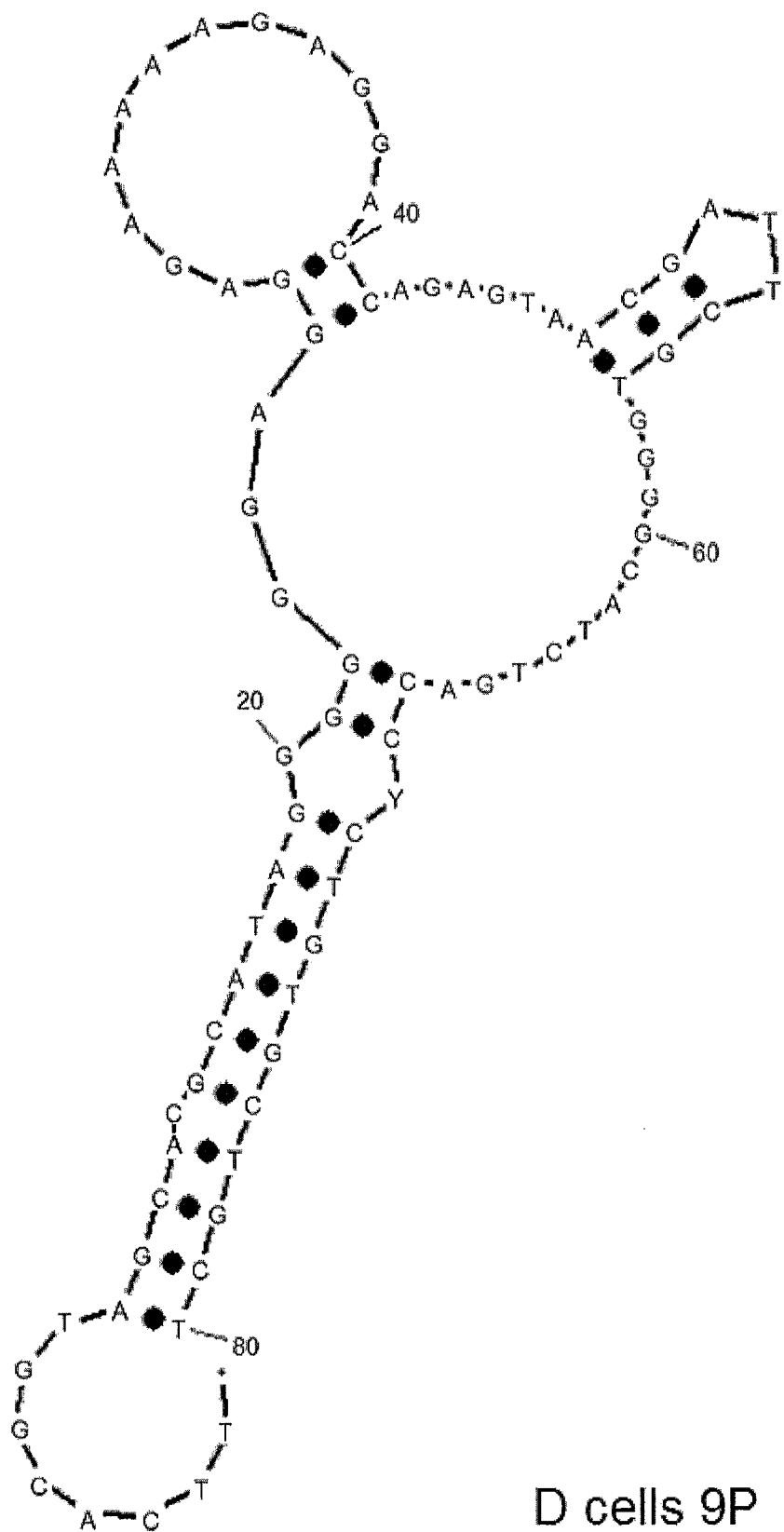
FIG. 19D    SEQ ID NO: 23

E CA 20  SEQ ID NO: 29

E CA 20P      SEQ ID NO: 30

APTAMERS SELECTED AGAINST LIVE S. PYOGENES CELLS

CROSS REFERENCE TO RELATED APPLICATIONS

This application claims the priority benefit of U.S. Provisional Application No. 61/468,706 filed on Mar. 29, 2011, entitled "Aptamers Selected Against Live S. Pyogenes Cells", the contents of which are incorporated herein by reference.

FIELD OF THE INVENTION

The present invention is directed to aptamers, methods and kits comprising same for detecting Streptococcus pyogenes.

BACKGROUND OF THE INVENTION

Aptamers are short oligonucleotides (single stranded DNA or RNA) which can form three-dimensional structures that specifically bind with high affinity and specificity to a wide range of targets including, for example, proteins, organic molecules, and inorganic molecules (Ellington and Szostak, 1990; Tuerk and Gold, 1990). The binding affinities of aptamers to proteins are similar or even higher than those of antibodies with typical dissociation constants ($K_d$ values) of micromolar to low picomolar range (Berezovski et al., 2005; Drabovich et al., 2005; Jensen et al., 1995; Mendonsa et al., 2005, 2005; Morris et al., 1998; Tuerk and Gold, 1990). Some aptamers exhibit femtomolar affinity.

Compared to antibodies, aptamers are easier to produce and inexpensive since the generation process occurs in vitro without the need for animals. In theory, aptamers can be generated against any target protein, and the binding target site of the protein can be determined. Once sequenced, aptamers can be synthesized at lower cost than antibodies, and may display lower cross-reactivity for a given target than an antibody. Aptamers can be easily modified with different chemical groups to enhance chemical properties such as stability or resolvability, and to achieve various functions. Aptamer coated surfaces can often be heated and reused.

The conventional approach for generating aptamers is through systematic evolution of ligands by exponential enrichment (SELEX) by which target-specific aptamers are selected and synthesized in vitro from a random aptamer library (Ellington and Szostak, 1990; Tuerk and Gold, 1990). SELEX typically involves incubation of ligand sequences with a target; partitioning of ligand-target complexes from unbound sequences via affinity methods; and amplification of bound sequences. In the incubation step, nucleic acid libraries are incubated with target molecules in an appropriate buffer at a desired temperature. After binding, the RNA/ssDNA aptamer-target complexes are separated from nonspecific molecules. Bound sequences are regenerated by enzymatic amplification processes. The amplified molecules are then used in the next round of selection. Selecting sequences which have the highest specificity and affinity against the target typically requires eight to twelve cycles. The selected oligonucleotides are analyzed for their sequences and structures after cloning and sequencing. After the sequence of an aptamer is determined, the aptamer can be easily generated through nucleic acid synthesis, and its binding affinity and specificity to a specific target can be validated. Aptamers may then be used in a variety of analytical, bioanalytical, therapeutic and diagnostic applications including, for example, protein identification and purification; inhibition of receptors or enzyme activities; and detection of proteins from bacteria in environmental or clinical samples.

Group A streptococcus (GAS) is implicated in a variety of ailments, including streptococcal pharyngitis, necrotizing fascitis, scarlet fever, streptococcal toxic shock syndrome, invasive systemic infections, and endocarditis (CDC, 2007). Usually throat and skin swabs, and wound aspirate from patients are tested. Point-of-care testing methodology relies upon either culture or antibody-based Rapid Antigen Detection (RAD), particularly a two-site sandwich immunoassay, to detect the Group A cell wall carbohydrate. Culture requires at minimum six to eight hours overnight incubation (Leung et al., 2006). In comparison, RAD is quicker, taking only minutes but having poor sensitivity and requiring a confirmatory culture step following negative results (Armengol et al., 2004). The sensitivity of culture and RAD is dependent upon the presence of a sufficient number of live cells in the inoculums.

An aptamer-based RAD test could negate the need for a confirmatory culture step, and may also provide lower cross-reactivity than antibody-based methods. In addition to replacing antibodies in RAD, aptamers against GAS cell surface molecules could prove useful in other assay formats. Current assay formats for bacterial detection using aptamers include enzyme-linked oligonucleotide assays, flow cytometry, chemiluminescent sandwich aptasensors, aptamer-quantum dot conjugates, and FRET-based assays (Bruno et al., 1999, 2002, 2010; Chen et al., 2007; Ikanovic et al., 2007; Fan et al., 2008; Hamula et al., 2008). The flexibility of aptamer reagents may enable the development of efficient, sensitive point-of-care diagnostic assays for GAS; for example, epidemiological surveillance of GAS clinical isolates is important for outbreak management, and vaccine development and implementation.

One of the major virulence factors of invasive GAS isolates (iGAS) is the M protein which is present on the bacterial surface (Beachey et al., 1981; Fischetti, 1991; Jones and Fischetti, 1988; Lancefield, 1962). While the M protein is a critical virulence factor for GAS, it can also be utilized as a typing marker for understanding the epidemiology of iGAS disease. The M protein can be typed serologically. Alternatively, GAS can be typed by sequencing of the gene which encodes the M protein, the emm gene (Beall et al., 2000; Whatmore et al., 1994). Currently, emm nomenclature extends from emm1 to emm124, with many emm types having minor variations in the nucleotide coding sequence resulting in emm subtypes for a particular emm type (Beall et al., 1996, 2000; Facklam et al., 1999; Neal et al., 2007). Different M-types are often, but not always, associated with different invasive infections; for example, M1 and M3 are more often associated with invasive infections than other M-types (Sharkawy et al., 2002; Vlaminckx et al., 2003).

Conventionally, GAS is M-typed via precipitin or latex agglutination methods, which involve screening bacterial surface extracts against different M-protein specific reference polyclonal antisera or antibodies conjugated to latex beads (Lancefield, 1933). Consistency between batches of typing sera is low (Facklam and Moody, 1968). Sequencing of the emm gene is replacing antibody-based typing methods and has expanded the repertoire of GAS emm types worldwide (Beall et al., 1996; Gardiner et al., 1995; Kaufhold et al., 1994; Saunders et al., 1997). Due to the complexity of such methods, the M typing of GAS isolates is conducted in laboratories specializing in GAS characterization. However, these methods are laborious and have low-throughput since each requires comparison of a bacterial isolate to a myriad of reference strains or databases.

The protein-based serotyping system of GAS makes it an ideal aptamer target. The M-protein contains a hypervariable N-terminus, to which typing antibodies bind to distinguish one M-type from another (Fischetti, 1989). Proteins are more successful SELEX targets than other smaller types of cell surface molecules such as carbohydrates and lipids. A SELEX technique has been developed against whole, live bacterial cells (Stoltenburg et al., 2007). Aptamers which bind to bacterial cell surface molecules using live *L. acidophilus* have been described (Hamula et al., 2008). However, the starting library diversity contained only $10^{12}$ to $10^{13}$ different sequences and required heat denaturation or streptavidin-biotin mediated separation to render the library and aptamer pools single-stranded.

SUMMARY OF THE INVENTION

The present invention is directed to aptamers, methods and kits comprising same for detecting *Streptococcus pyogenes*.

In one aspect, the invention comprises a method of screening a subject for *Streptococcus pyogenes* comprising the steps of:
a) obtaining a body sample from the subject;
b) contacting the sample or a bacterial culture of the sample with an aptamer or a panel of aptamers specific to *S. pyogenes*;
c) detecting the presence or absence of *S. pyogenes* in the sample or the bacterial culture, wherein binding of the aptamer or the panel of aptamers is indicative of the presence of *S. pyogenes*.

In one embodiment, the sample is selected from urine, blood, plasma, serum, saliva, a throat swab, a skin swab, wound aspirate, ocular fluid, spinal fluid, or perspiration.

In one embodiment, the aptamer is specific to a plurality of M-type strains of *S. pyogenes*. In one embodiment, the M-type strains comprise M1, M2, M3, M4, M5, M6, M11, M12, M28, M41, M49, M59, M75, M77, M82, M83, M89, M91, M92, and M114.

In one embodiment, the aptamer comprises the nucleic acid sequence as set forth in any one of SEQ ID NOS: 1-32, or a nucleic acid sequence having at least 80%, at least 85%, at least 90%, at least 95%, at least 96%, at least 97%, at least 98%, or at least 99% sequence identity therewith. In one embodiment, the aptamer comprises the nucleic acid sequence as set forth in SEQ ID NO: 9, SEQ ID NO: 13 or SEQ ID NO: 15.

In one embodiment, the aptamer is specific to *S. pyogenes* M11. In one embodiment, the aptamer comprises the nucleic acid sequence as set forth in any one of SEQ ID NOS: 16-32, or a nucleic acid sequence having at least 80%, at least 85%, at least 90%, at least 95%, at least 96%, at least 97%, at least 98%, or at least 99% sequence identity therewith. In one embodiment, the aptamer comprises the nucleic acid sequence as set forth in SEQ ID NO: 29, SEQ ID NO: 30 or SEQ ID NO: 32.

In one embodiment, the aptamer has a binding dissociation constant less than or equal to 100 nM. In one embodiment, the aptamer has a binding dissociation constant less than or equal to 10 nM.

In one embodiment, the aptamer comprises single or double-stranded DNA. In one embodiment, the aptamer comprises single or double-stranded RNA.

In one embodiment, before step (b), the aptamers are selected using SELEX comprising a mixture of whole bacterial cells. In one embodiment, the aptamer is labeled with a fluorescent compound.

In another aspect, the invention comprises an isolated nucleic acid having the nucleic acid sequence as set forth in any one of SEQ ID NOS: 1-32, or having at least 80%, at least 85%, at least 90%, at least 95%, at least 96%, at least 97%, at least 98%, or at least 99% sequence identity therewith.

In another aspect, the invention comprises a kit for detecting the presence of *S. pyogenes* comprising an aptamer or a panel of aptamers, reagents for detecting the binding of the aptamer or panel of aptamers to *S. pyogenes*, and one or more supports.

In yet another aspect, the invention comprises a method of screening a subject for Group B *Streptococcus* comprising the steps of:
a) obtaining a body sample from the subject;
b) contacting the sample or a bacterial culture of the sample with an aptamer comprising the nucleic acid sequence as set forth in SEQ ID NO: 6 or SEQ ID NO: 21;
c) detecting the presence or absence of Group B *Streptococcus* in the sample or the bacterial culture, wherein binding of the aptamer is indicative of the presence of Group B *Streptococcus*.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described by way of an exemplary embodiment with reference to the accompanying simplified, diagrammatic, not-to-scale drawings. In the drawings:

FIGS. 10A-F are schematic diagrams showing binding dissociation constants ($K_d$) and predicted secondary structures of high affinity and specific aptamer sequences (SEQ ID NOS: 9, 8, 13, 10, 11 and 15, respectively) for a mixture of ten different S. pyogenes M-types used in SELEX.

FIGS. 19A-F are schematic diagrams showing the predicted structures of aptamer sequences (SEQ ID NOS: 31, 32, 22, 23, 29, and 30, respectively) with high affinity and selectivity for S. pyogenes M11.

DETAILED DESCRIPTION OF PREFERRED EMBODIMENTS

Figure 1:
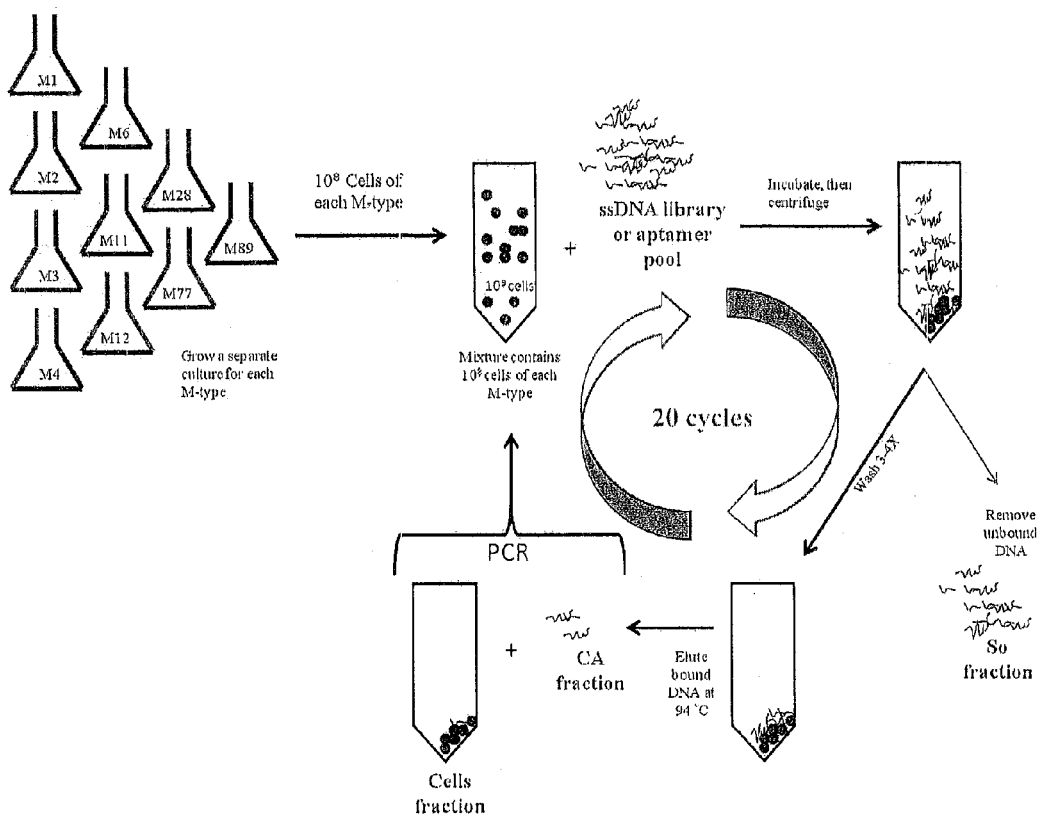
FIG. 1 is a schematic diagram showing a bacterial cell SELEX method against a mixture of ten GAS M-types.

The present invention is directed to aptamers, methods and kits comprising same for detecting Streptococcus pyogenes. When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

The present invention is directed to aptamers, methods and kits comprising same for detecting Streptococcus pyogenes in a sample. As used herein, the terms "aptamer" or "aptamer sequence" mean single or double-stranded nucleic acids (such as RNA or DNA) whose distinct nucleotide sequence determines the folding of the molecule into a unique three dimensional structure. In one embodiment, the aptamers comprise single or double-stranded DNA or RNA sequences.

In one embodiment, the aptamer is specific to a plurality of M-type strains of S. pyogenes. In one embodiment, the M-type strains comprise M1, M2, M3, M4, M5, M6, M11, M12, M28, M41, M49, M59, M75, M77, M82, M83, M89, M91, M92, and M114.

In one embodiment, the aptamer comprises the nucleic acid sequence as set forth in any one of SEQ ID NOS: 1-32. In one embodiment, the aptamer comprises the nucleic acid sequence as set forth in SEQ ID NO: 9, SEQ ID NO: 13 or SEQ ID NO: 15.

In one embodiment, the aptamer is specific to S. pyogenes M11. In one embodiment, the aptamer comprises the nucleic acid sequence as set forth in any one of SEQ ID NOS: 16-32. In one embodiment, the aptamer comprises the nucleic acid sequence as set forth in SEQ ID NO: 29, SEQ ID NO: 30 or SEQ ID NO: 32.

Nucleic acid sequences having at least 80% homology, more preferably at least 85% homology, more preferably at least 90% homology, more preferably at least 95% homology, or more preferably at least 96%, 97%, 98%, or 99% homology with any of the nucleic acid sequences described herein are within the scope of this invention. Accordingly, in one embodiment, the aptamer comprises a nucleic acid sequence having at least 80%, at least 85%, at least 90%, at least 95%, at least 96%, at least 97%, at least 98%, or at least 99% sequence identity to any one of SEQ ID NOS: 1-32. Methods for isolation of such nucleic acid sequences are well known in the art (Ausubel et al., 1995).

In one embodiment, the invention comprises an isolated nucleic acid having the nucleic acid sequence as set forth in any one of SEQ ID NOS: 1-32, or having at least 80%, at least 85%, at least 90%, at least 95%, at least 96%, at least 97%, at least 98%, or at least 99% sequence identity therewith. As used herein, the term "isolated" means that a substance or a group of substances is removed from the coexisting materials of its natural state.

In one embodiment, the aptamer binds with high affinity and selectivity or is specific to a plurality of M-type strains of S. pyogenes. In one embodiment, the aptamer binds with high affinity and selectivity specifically to S. pyogenes M11. As used herein, the term "binding" means that the aptamers of the present invention have affinity for Streptococcus. As used herein, the term "specific," when used in reference to binding, means that the binding between the aptamer and Streptococcus is such that it can be distinguished from non-specific binding to other molecules and cells in an assay. Appropriate controls can be used to distinguish between "specific" and "non-specific" binding. It will be appreciated by those skilled in the art that binding between the aptamer and Streptococcus may be detected using a label. As used herein, the term "label" means a chromogen, catalyst, fluorescent compound, chemiluminescent compound, colloidal gold, a dye particle, a latex particle tagged with a detector reagent such as, for example, a colored or fluorescent dye, and the like. In one embodiment, the label is a fluorescent compound.

In one embodiment, the invention comprises a method of screening a subject for *Streptococcus pyogenes* comprising the steps of:

a) obtaining a body sample from the subject;
   b) contacting the sample or a bacterial culture of the sample with an aptamer or a panel of aptamers specific to *S. pyogenes*;
   c) detecting the presence or absence of *S. pyogenes* in the sample or the bacterial culture, wherein binding of the aptamer or the panel is aptamers is indicative of the presence of *S. pyogenes*.

As used herein, the term "sample" means a sample which may contain *S. pyogenes*. A sample may comprise a body sample (for example, urine, blood, plasma, serum, saliva, a throat swab, a skin swab, wound aspirate, ocular fluid, spinal fluid, perspiration, and the like) from a subject, or a bacterial culture of the body sample. In the event that the bacterial count might be low, a body sample may be incubated in a suitable broth for bacterial growth. The cells which grow can be subsequently tested with an aptamer or a panel of aptamers. As used herein, the term "subject" means humans or animals. The panel of aptamers may be used to provide a "yes" or "no" result (i.e., the subject is either "positive" or "negative" for *S. pyogenes*). An aptamer may be specific to solely one particular strain of *S. pyogenes*, such as, for example, *S. pyogenes* M11. It will be appreciated by those skilled in the art that the method of the present invention has diagnostic and therapeutic applications, including screening for *S. pyogenes* and monitoring the progress of treatment for *S. pyogenes*.

The following is a specific example of one embodiment of the present invention. This example demonstrates how the method of the present invention can be used in screening for *S. pyogenes* using a panel of aptamers. This example is offered by way of illustration and is not intended to limit the invention in any manner.

Bacterial-cell SELEX was used to generate aptamers specific to *S. pyogenes* and having antibody-level affinities and selectivities. Using whole live bacterial cells as targets in SELEX negates the need for a priori purification of specific target molecules from the bacterial surface (Chen et al., 2007; Cao et al., 2009; Dwivedi et al., 2010; Hamula et al., 2008). Prior reports have used one cell type at a time, usually a monoclonal population.

In comparison, the method of the present invention uses a mixture of bacterial types in order to broaden aptamer selectivity. Consequently, the resultant aptamer pool contained sequences which are specific to *S. pyogenes* and can detect several M-types. Species cross-reactivity can thus be obtained (White et al., 2001). Similarly, aptamer selectivity and specificity for a cell type can be refined by conducting counterselection steps against a non-target cell to remove unwanted sequences (Sefah et al., 2010)

Accordingly, a mixture containing ten Group A *Streptococcus* (GAS) M-types, namely M1, M2, M3, M4, M6, M11, M12, M28, M77, and M89, was used (Tyrrell et al., 2002). GAS is an ideal candidate for aptamer selection due to its well-characterized surface and protein-based serotyping system. The resultant aptamers bound strongly and specifically to all ten M-types and to ten non-target M-types. Two aptamers, 20A24P and 15A3P (with estimated binding dissociation constants of 9 and 10 nM, respectively) have potential for incorporation into rapid antigen detection tests.

Figure 2:
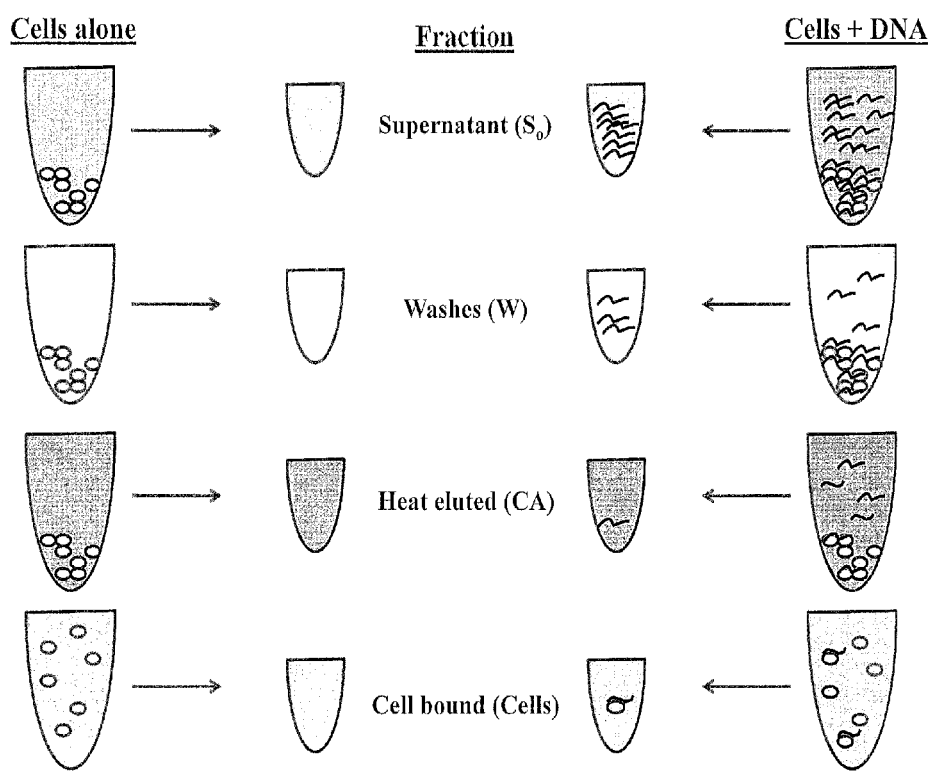
FIG. 2 is a schematic diagram showing fractions collected from SELEX using GAS and control.
Figure 3:
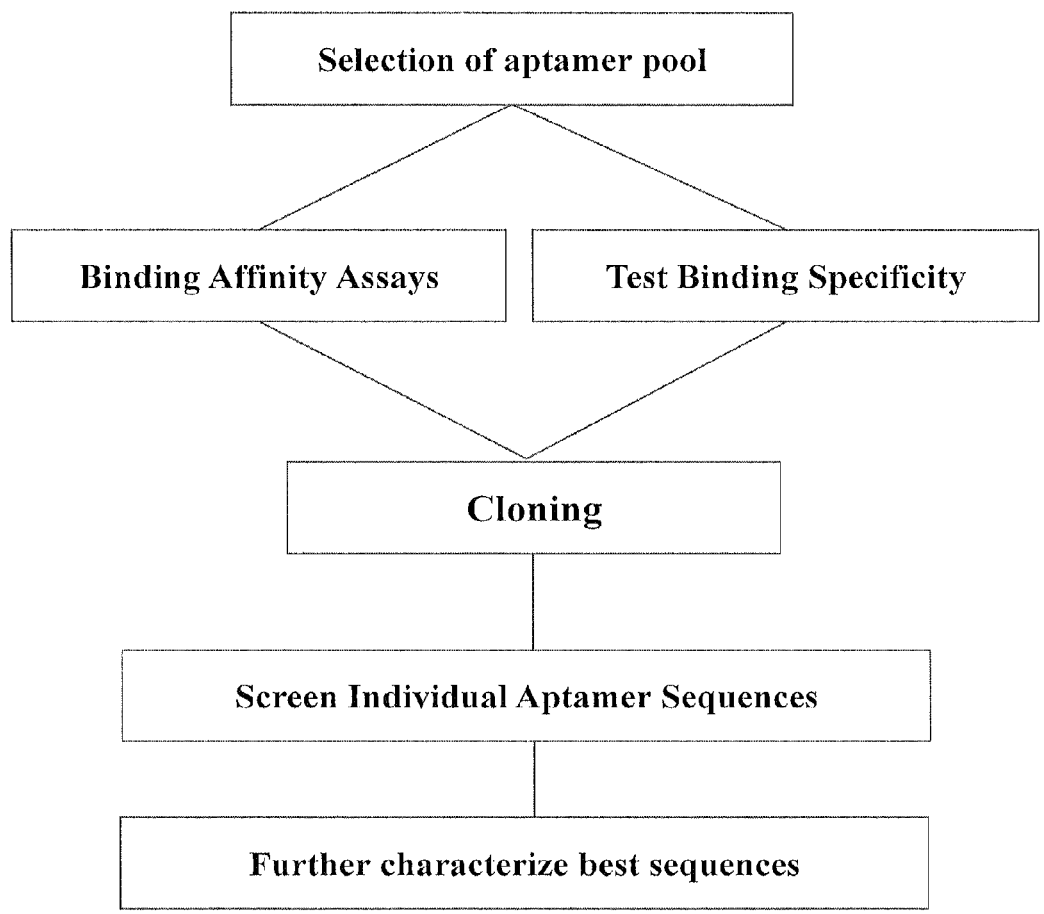
FIG. 3 is a schematic diagram showing a process for screening the aptamer pools from each round of SELEX and for characterization of individual sequences.

FIGS. 1-3 illustrate the method of the present invention. A mixture containing an equal number of cells from each of the ten *S. pyogenes* M-types was used as a target (FIG. 1). A randomized oligonucleotide library was incubated with the cell mixture. Cells were partitioned via centrifugation. Fractions representing the incubation supernatant ("$S_0$"), washes ("W"), heat-eluted cell-bound aptamers ("CA"), and cell-bound aptamers ("Cells") were collected and amplified following incubation (FIG. 2), While the majority of the DNA was retained in the supernatant fraction, a substantial amount of DNA adhered to the cells even after the third wash. The number of washes was increased to four at which point cell-bound DNA was no longer detectable via PCR. The aptamers were heat eluted from the cells at high temperature in low salt ("CA" fraction). Even after heat elution, some sequences remained bound to the cells. The CA fraction and the cells were amplified for use as inputs in the next round of SELEX. A negative control consisting of cells without added DNA library was run concurrently, Twenty rounds of SELEX were conducted.

The amplification products of the CA fraction (FIG. 4, lane 13) represent the DNA sequences strongly bound to the cells. The single 80-bp band after each round of selection and PCR amplification of the CA and Cells fractions suggests that the cells were able to bind to a pool of aptamer sequences. No DNA was amplified from the wash or CA/Cells fractions of the negative control, which consisted of cells treated to the incubation, wash and heat elution procedures without the addition of library or aptamer pool DNA. The gel photographs for SELEX 2A to 20A were similar in that the So, W, CA, and Cells fractions were all collected and PCR amplified (data not shown).

The binding affinity and selectivity of aptamer pools following each round of selection were determined. Flow cytometric analyses of incubation mixtures containing fluorescently-labeled aptamer pools and the target cell mixture were carried out to assess changes in affinity of the aptamer pools for *S. pyogenes*. An increase in the number of fluorescent cells was due to the increased binding of the fluorescent aptamers to the target cells. Negative controls consisting of cells alone and target cells incubated with fluorescently-labeled randomized library were carried out concurrently. Controls conducted using fluorescent aptamer pools alone and buffer with BSA and tRNA alone did not yield any increase in gated fluorescence above background levels (data not shown).

Figure 5:
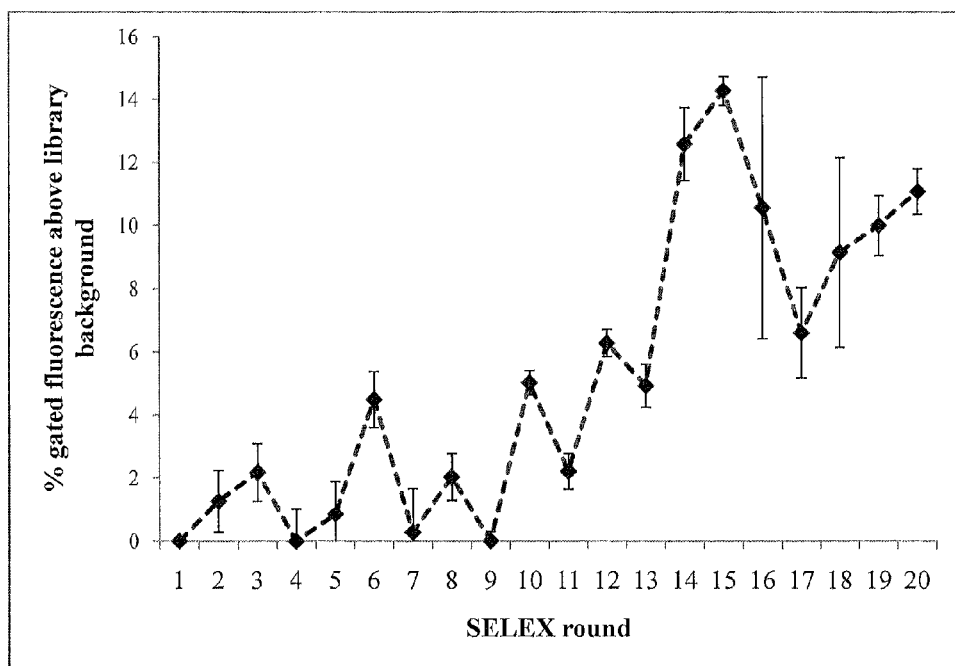
FIG. 5 is a graph of the average percent gated fluorescence intensity of *S. pyogenes* M-type mixture incubated with fluorescently-labeled aptamer pools after increasing SELEX rounds.

With increasing rounds of selection, the percent of cells with fluorescence above library background increased to a maximum average of 14% at round 15 for SELEX A aptamer pools (FIG. 5). For SELEX A, aptamer pool binding did not start to increase above background until round 10. The percent of cells with fluorescence above library decreased from 14% at round 15 to 7% at round 17 before increasing again to 11% at round 20. Aptamer pools from the $15^{th}$ and $20^{th}$ rounds of SELEX A displayed the highest affinity for the target cells when screened via flow cytometry.

Without being bound by theory, variability in aptamer pool binding may be attributed to differences in expression of cell surface molecules between and within M-types. Since the SELEX target is a mixture of different M-types, it is much more complex than a monoclonal population. Small day-to-day variations in the surface of each M-type may be additive, resulting in high overall variability. Differences in cell surface molecule expression and protein synthesis are greatest when cells are grown in logarithmic phase (Kolter et al., 1993), at which they were harvested for selection. Support for this theory resides in the results of separate screenings of the aptamer pools against each M-type. Duplicate incubations set up using cells from two separate colonies show substantial variability in aptamer pool binding (data not shown). This variability is minimal when duplicates from the same culture or duplicates of two separate stationary phase cultures are analyzed (data not shown). Screening aptamer pools against stationary phase cultures thus resulted in decreased variability of aptamer pool binding.

The aptamer pools were cloned and sequenced to obtain fifty-seven sequences. All sequences were analyzed both with and without primers. Minimal sequence repetition was found, with many sequences containing high GC content indicative of secondary structure formation (Table 1). Within the SELEX A round 15 pool, sequences 15A2 and 15A15 are identical, as are sequences 15A8, 15A16 and 15A17. For the SELEX A round 20 pool, 20A6, 20A15, and 20A17 are identical, as is 15A10. Sequences were chosen for further screening based upon their repetitiveness, predicted secondary structures, and free energies of formation (data not shown).

TABLE 1

Sequences repeated within and between aptamer pools 15A and 20A.

| Occurrence | Sequence |
| --- | --- |
| 15A2, 15A15 | 5'-GAC ACC AAG CTA AGA TCG TAA TGT TGG TGG TAC ACT TCG G-3' (SEQ ID NO: 1) |
| 15A 8, 15A16, 15A17 | 5'-GGT CCA AGG TTA TAT CGA AGT GGC CTG CAG CCT GCA ACG G-3' (SEQ ID NO: 2) |
| 15A10, 20A6, 20A15, 20A17 | 5'-CCC ACC CCC GTC ACT TCC TTC TTC CCG GTG TCT CCA CGT C-3' (SEQ ID NO: 3) |

The binding of individual aptamer sequences to a target cell mixture was assessed. Each species tested consisted of a mixture of separate strains, with each strain being cultured separately and combined immediately prior to selection. Fluorescently-labeled aptamer sequences were incubated with the target mixture of the ten *S. pyogenes* M-types used for selection (200 pmole of aptamer:$10^8$ cells) and analyzed via flow cytometry. Aptamer sequences obtained after round 20 of SELEX A appeared to have the highest affinity for the *S. pyogenes* M-type mixture. Nine sequences from the pool had greater than 50% gated fluorescence intensity above a randomized library control (Table 2).

TABLE 2

Screened aptamer sequences with and without primers

| Name | Sequence |
| --- | --- |
| 20A1 | 5' FAM/CAGAACGCACCCGCACACCTCCATCACTCGCATGCACCCC-3' (SEQ ID NO: 4) |
| 20A1P | 5' FAM/<u>TTC ACG GTA GCA CGC ATA GG</u> CAGAACGCACCCGCACACCTCCATCACTCG CATGCACCCC <u>CAT CTG ACC TCT GTG CTG CT</u>-3' (SEQ ID NO: 5) |
| 20A8 | 5' FAM/CCCCACGAATCGTTACTCTGGTCCTCTATTTCTCCTCCC C-3' (SEQ ID NO; 6) |
| 20A8P | 5' FAM/<u>AGC AGC ACA GAG GTC AGA TG</u> CCCCACGAATCGTTACTCTGGTCCTCTATT TCT CCTCCCC <u>CCT ATG CGT GCT ACC GTG AA</u>-3' (SEQ ID NO: 7) |
| 20A9 | 5' FAM/CACACGCTGAAGAAACTGAGGTCGTAGGTTTTCTTCGGG-3' (SEQ ID NO; 8) |
| 20A9P | 5' FAM/<u>AGC AGC ACA GAG GTC AGA TG</u> CACACGCTGAAGAAACTGAGGTCGTAGGTTTT CTTCGGG <u>CCT ATG CGT GCT ACC GTG AA</u>-3' (SEQ ID NO: 9) |
| 20A12P | 5' FAM/<u>TTC ACG GTA GCA CGC ATA GG</u> GCCCGACACTCGTCCACCCGATACC TCT CATGTGTCCC <u>CAT CTG ACC TCT GTG CTG CT</u>-3' (SEQ ID NO: 10) |
| 20A14P | 5' FAM/<u>AGC AGC ACA GAG GTC AGA TG</u> GGCATGGGAAGAGAAAG CGGGATAACTTCGTT ACCGGGC <u>CCT ATG CGT GCT ACC GTG AA</u>-3' (SEQ ID NO: 11) |
| 20A24 | 5' FAM/GGG GGA AGA CAC AGA GAA AGG CCG GGG TGA AGT GTA GAG G-3' (SEQ ID NO: 12) |
| 20A24P | 5' FAM/<u>AGC AGC ACA GAG GTC AGA TG</u> GGG GGA AGA CAC AGA GAA AGG CCG GGG TGA AGT GTA GAG G<u>CCT ATG CGT GCT ACC GTG AA</u>-3' (SEQ ID NO: 13) |
| 15A3 | 5' FAM/GAC AGC AAG CCC AAG CTG GGT GTG CAA GGT GAG GAG TGG G-3' (SEQ ID NO: 14) |
| 15A3P | 5' FAM/<u>TTC ACG GTA GCA CGC ATA GG</u> GACAGCAAGCCCAAGCTGGGTGTGCAAGGT GAG GAGTGGG <u>CAT CTG ACC TCT GTG CTG CT</u>-3' (SEQ ID NO: 15) |

Figure 6:
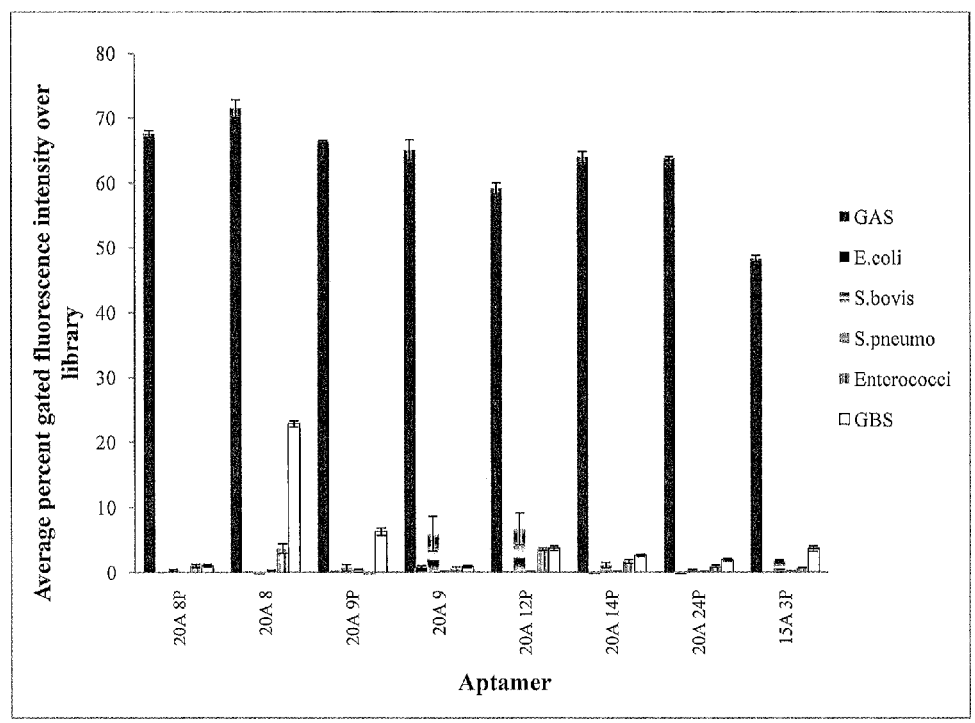
FIG. 6 is a graph showing screening of sequences from SELEX 15A and 20A aptamer pools against different types of bacterial cells.

Sequences 20A1, 20A1P (with primers), and 20A8 were the highest binders with gated fluorescence above background values of around 72%. The highest binding sequence in the 15A pool is 15A3P with a gated fluorescence above background of 48% (FIG. 6).

Sequences 20A1, 20A8, and 20A9 form hairpins both in the absence and presence of the primer sequences (data not shown). The affinity of these aptamers for the *S. pyogenes* mixture changed minimally upon inclusion or exclusion of primers in the sequence. The affinity remained at 72% gated fluorescence intensity above library for both 20A1 and 20A1P, decreased from 72% for 20A8 to 68% for 20A8P, and increased from 65% for 20A9 to 66% for 20A9P (FIG. 6). However, not all non-hairpin sequences have low affinity for the target cells. Sequence 20A24P forms a branched structure with high affinity for the target cell mixture (gated fluorescence intensity above library of 64%). Removal of the primers negates this affinity (8%). The sequence 20A24 forms a hairpin. Sequences with no or minimal affinity for the target cells tended to have minimal predicted secondary structures (data not shown).

The selectivity of high affinity aptamers for *S. pyogenes* was determined. Fluorescently-labeled aptamer sequences 20A8, 20A8P, 20A9, 20A9P, 15A3P, 20A24P, 20A12P and 20A14P were tested against a variety of other bacteria including pathogens and commensal flora that could interfere with a diagnostic test (Table 3). Binding to other species of *Streptococcus* was tested using non-pathogenic *S. bovis*, and the pathogens *S. pneumoniae* and *S. agalactiae* (Group B *Streptococcus* or GBS). *Escherichia coli* DH5α was used to assess aptamer binding to a representative gram negative organism. Sequences were also screened against the human flora *Enterococcus* sp. For the *S. pneumoniae*, *S. agalactiae*, and *Enterococcus* isolates, mixtures were prepared containing an equal number of cells from multiple isolates, as were the *S. pyogenes* mixtures used for selection.

Figure 7:
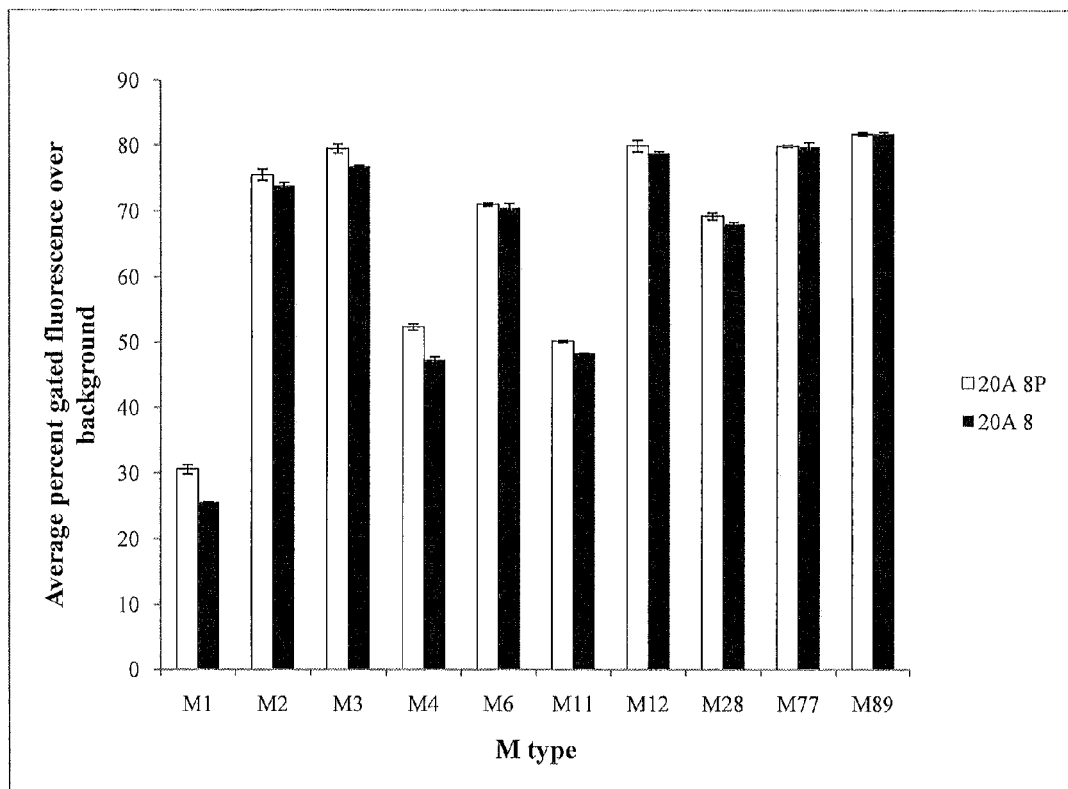
FIG. 7 is a graph showing binding of aptamer sequences to separate M-types, with 200 pmole of each aptamer sequence having been screened against $10^9$ cells of each M-type separately, not as a mixture.
Figure 8A:
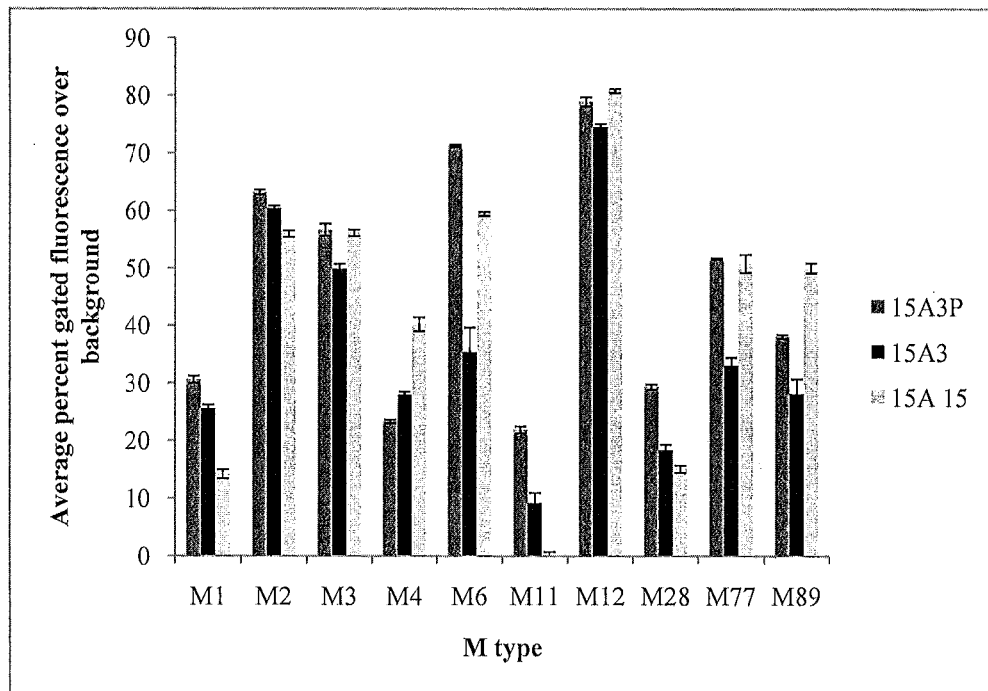
FIGS. 8A and 8B are graphs showing binding of medium affinity (FIG. 8A) and low affinity (FIG. 8B) aptamer sequences to separate M-types.
Figure 8B:
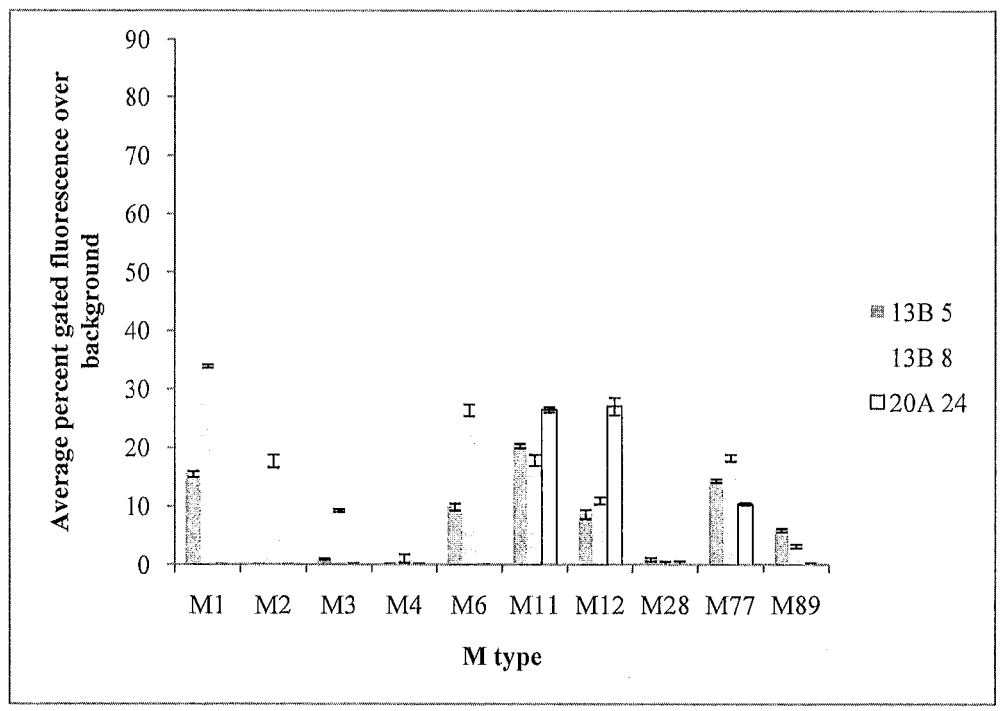

Fluorescently-labeled individual aptamer sequences were also screened via flow cytometry against separate *S. pyogenes* M-types. None of the aptamer sequences tested were M-type specific. The affinity of a given sequence for the *S. pyogenes* mixture appears to mirror its affinity for the separate M-types; for example, aptamer sequences with high affinity to the 10 M-type mixture exhibited high binding to most of the M-types tested separately. Sequences 20A8 and 20A8P have very similar affinities for a given M-type, with percent gated fluorescence above background above 50% for all M-types except M1. M-types M2, M3, M6, M12, M77 and M89 have gated fluorescence above background greater than 70% (FIG. 7). The high affinity sequences 20A24P and 15A3P showed a similar trend (data not shown). This trend of aptamer affinity for the target cell mixture mirroring aptamer affinity for individual M-types is also true of sequences with medium and low affinities (FIGS. 8A-B). The presence or absence of primers had little effect on GAS or M-type affinity of sequence 20A8/20A8P, indicating that the hypervariable region in the center of the aptamer sequence is responsible for binding (FIG. 7).

Figure 9:
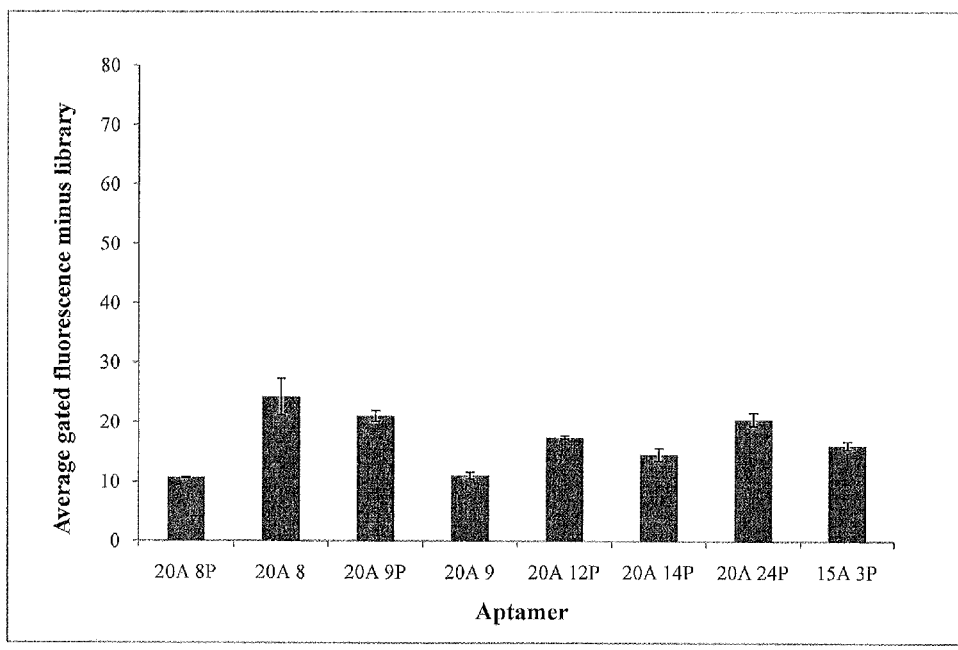
FIG. 9 is a graph showing binding of aptamer sequences to a mixture of S. pyogenes M-types (M5, M41, M49, M59, M75, M82, M83, M91, M92, and M114) not used as targets during selection.
Figure 10A:
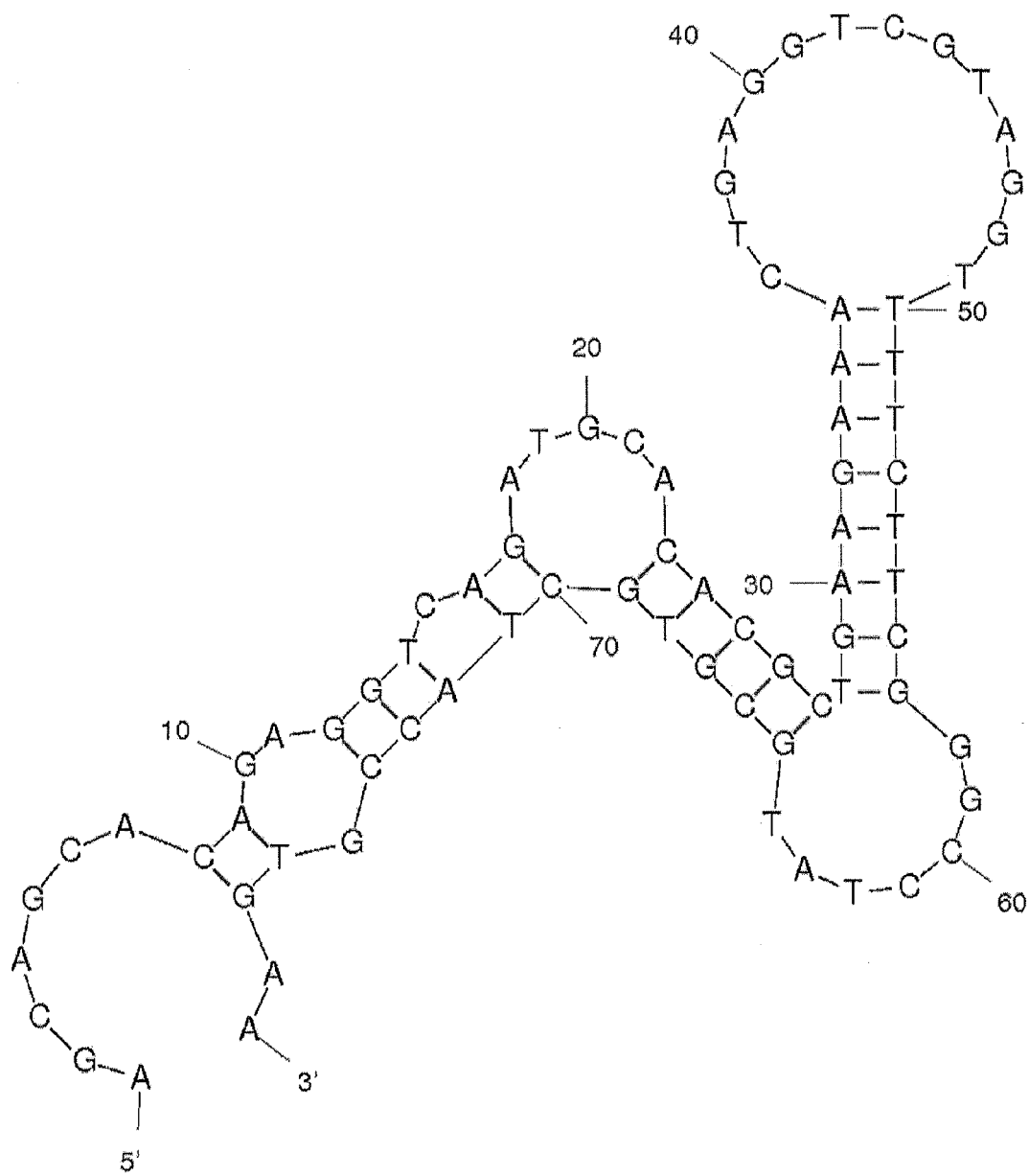
Figure 10B:
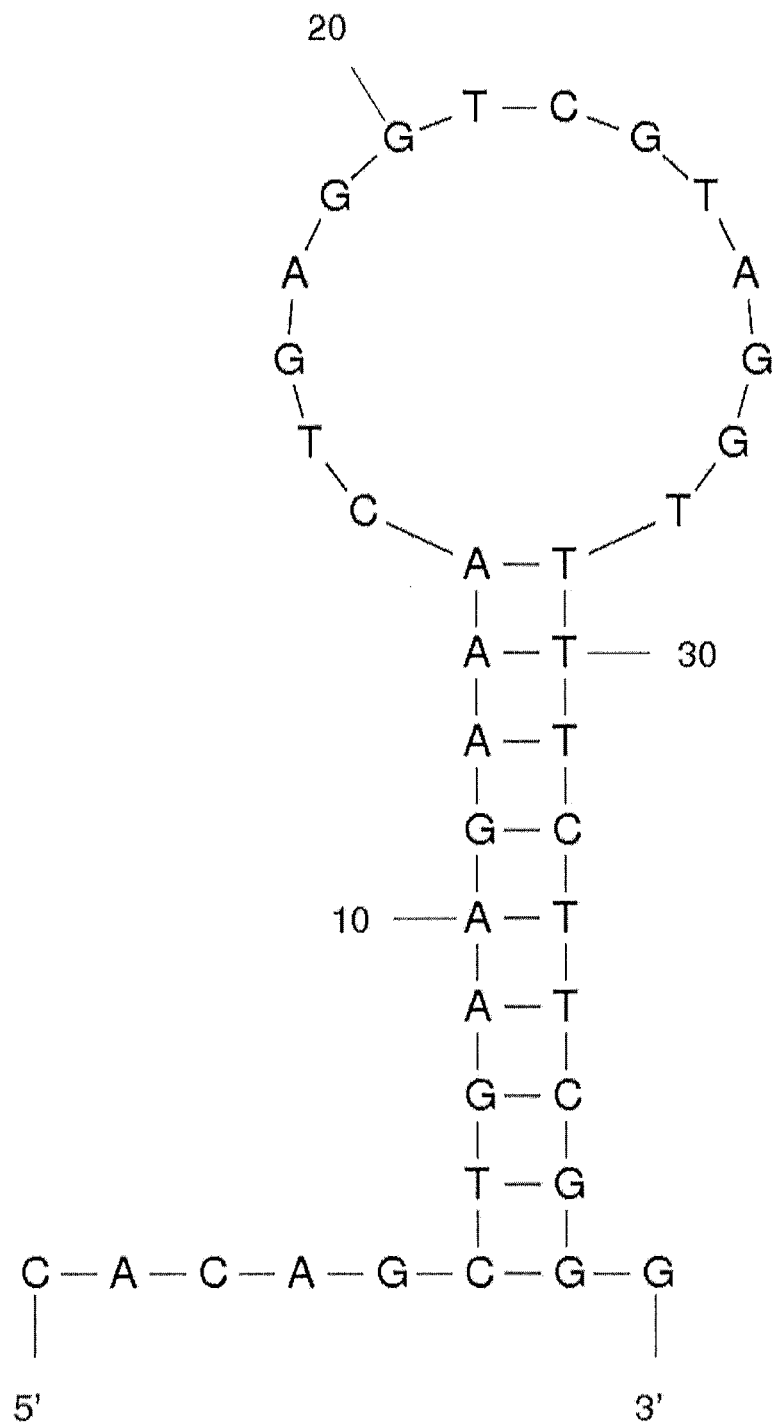
Figure 10C:
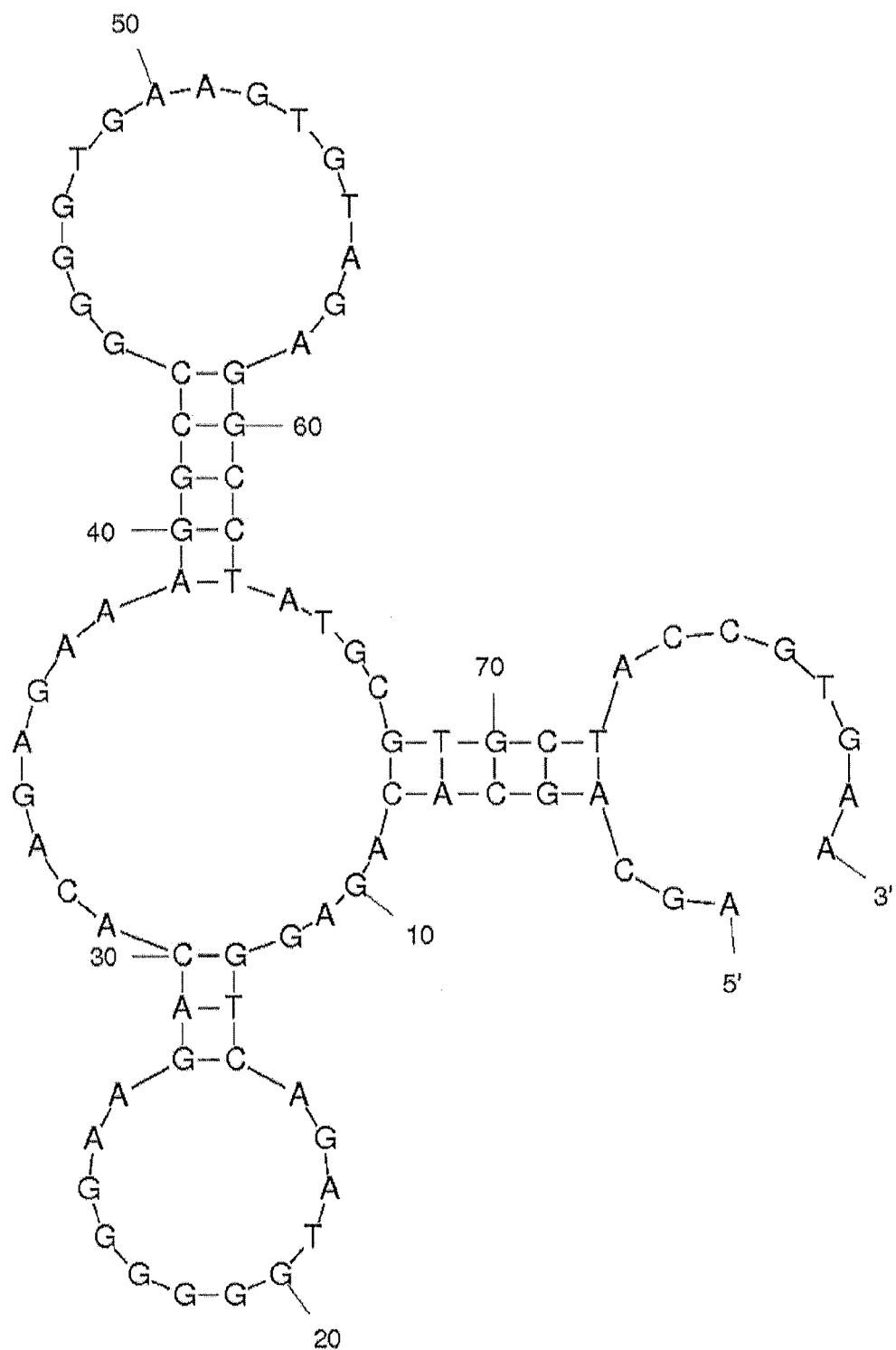
Figure 10D:
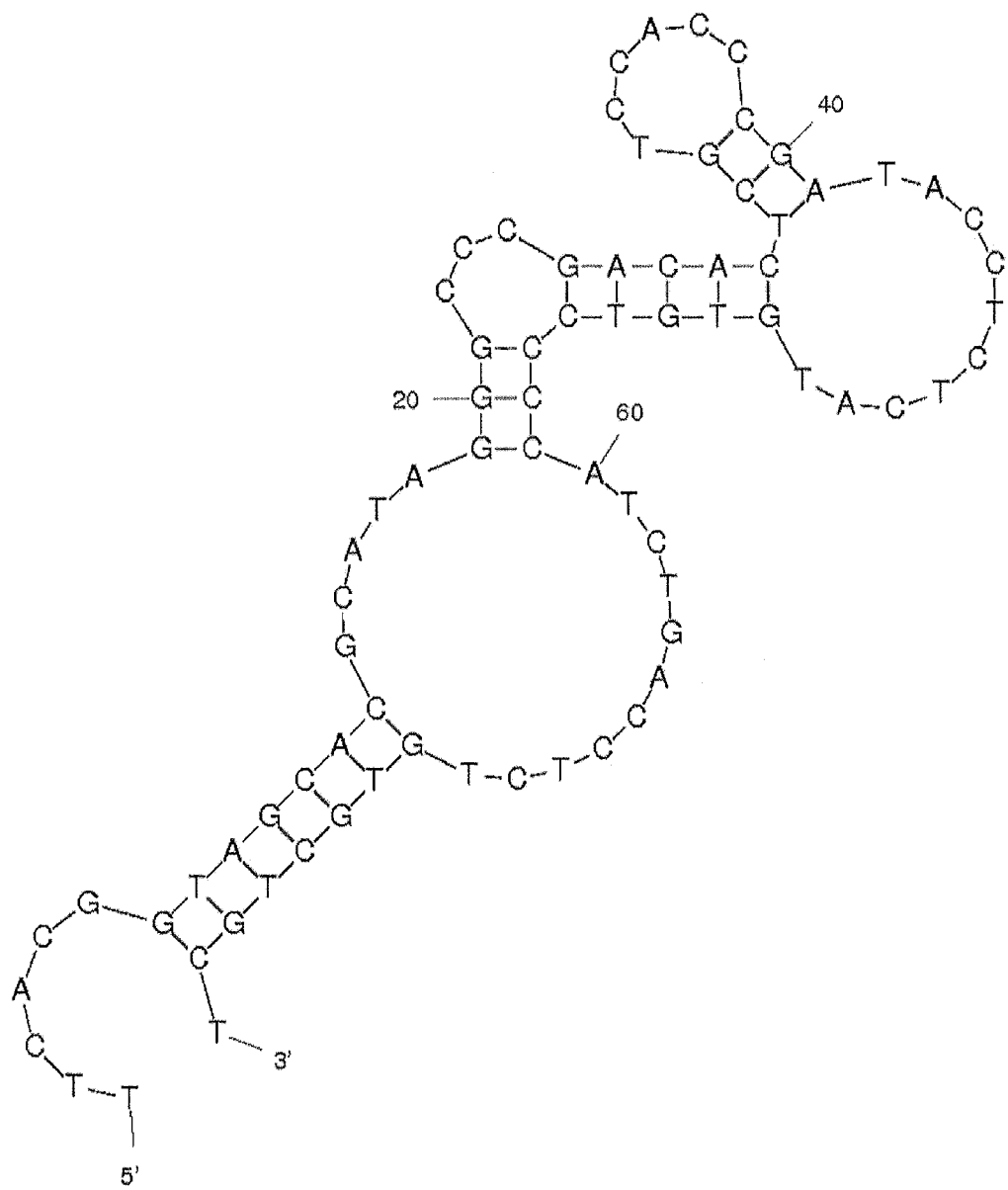
Figure 10F:
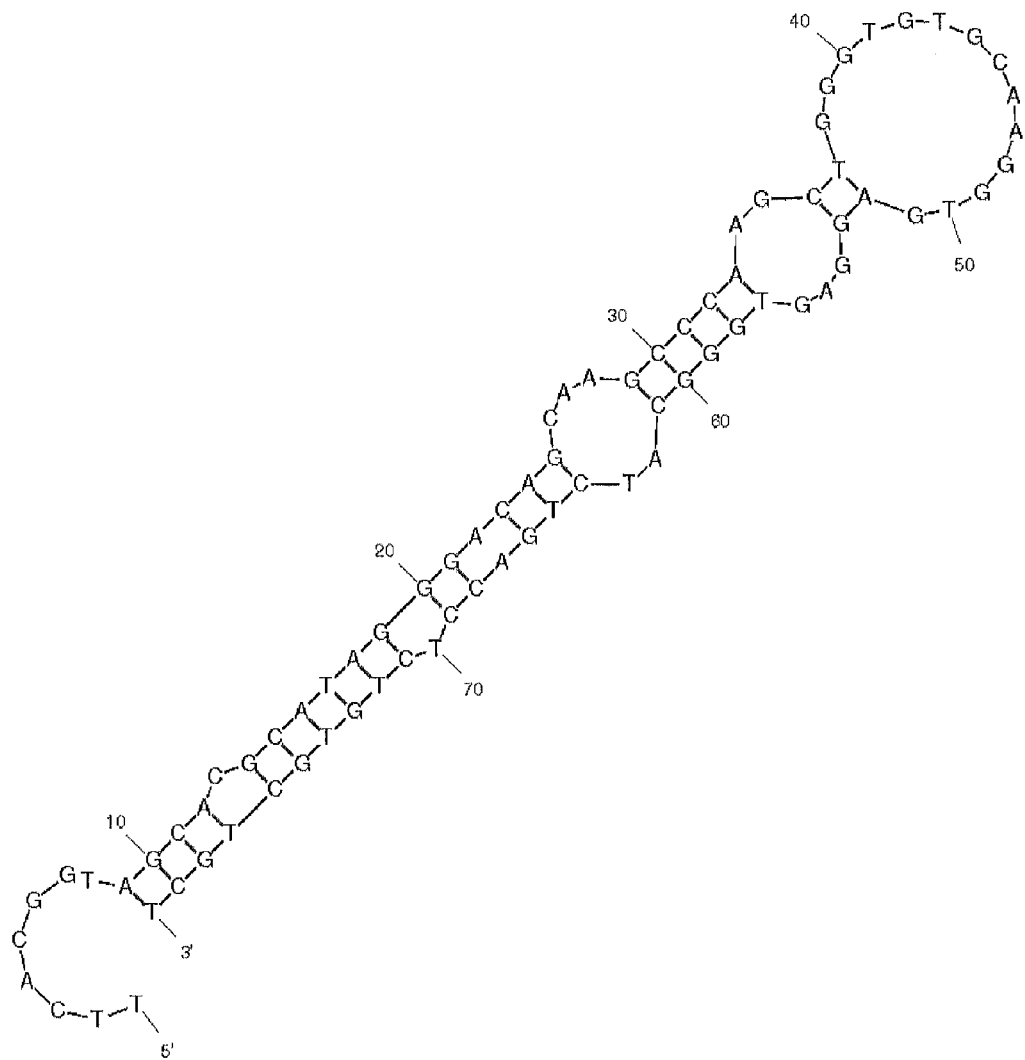

The tested aptamer sequences also bound *S. pyogenes* M-types other than the ten used for SELEX. A cell mixture containing ten M-types (M5, M41, M49, M59, M75, M82, M83, M91, M92, and M114) not used for selection was tested (FIG. 9; 200 pmole of each fluorescently-labeled aptamer incubated with a mixture of $10^8$ total cells). Binding to this mixture was observed for all sequences tested, ranging from 23% for 20A8 to 1% for 20A9. Without being bound by theory, the selection appeared to generate aptamer pools containing a mixture of sequences of similar affinity for all target M-types, and cross-reactivity to non-target M-types. The aptamers may thus be used together to identify strains of GAS based on the binding pattern produced. Multiple cell-specific aptamers have been used together as a panel for flow cytometric identification and typing of cancer cells, *Staphylococ-*

TABLE 3

| Species, isolates and strains for testing selectivity of aptamers to *S. pyogenes* | |
| --- | --- |
| *Streptococcus agalactiae* | 975R547 IV; JM9 VIII; 7271 VII; 975R390 VI; 965R400 Ia; 975R384 V; 12351 IV; 965R155 Ia; 975R938 II; 975R27 Ib; 975R331 IV; 955R2028 IV; 975R591; 975R138 II; 975R570 Ib; 975R104 VIII; 9842 VI; 975R594 III |
| *Streptococcus pneumoniae* | 4; 6B; 9V; 14; 18C; 19F; 23F; 19A; 5; 6A |
| *Streptococcus bovis* (ATCC #) | 33317 |
| *Enterococcus* sp.(ATCC #) | *E. saccharolyticus* (43076); *E. raffinosous* (49447); *E. pseudoarium* (49372); *E. mundtii* (43186); *E. malodoratus* (43197); *E. hirap* (8043); *E. gallinarium* (49573); *E. faecium* (19434); *E. faecalis* (19433); *E. durans* (19432); *E. cecorum* (43198); *E. casselflavus* (25788); *E. avium* (14025) |
| *Escherichia coli* | DH5α |

None of the GAS-specific sequences bound strongly to any of the other species tested, with the exception of 20A8 which appeared to have affinity for the GBS mixture (FIG. 6). However, this affinity was low in comparison to the *S. pyogenes* target cell mixture. The percent gated fluorescence intensity above library background was 23% when 20A8 was incubated with GBS cells and 72% when incubated with the original *S. pyogenes* target cell mixture, a three-fold difference which may or may not interfere in a diagnostic test. Inclusion of the primer sequences (20A8P) seems to negate GBS binding, bringing the percent gated fluorescence intensity above library background down to 1%. The same sequence (20A8P) binding to the target GAS cells yielded 68% gated fluorescence above background.

*cus aureus*, and vaccinia-infected tissue culture cells (Cao et al., 2009; Shangguan et al., 2007; Tang et al., 2007, 2009).

The binding affinity dissociation constants ($K_d$) of high affinity aptamer sequences were estimated. Binding saturation flow cytometric analysis was carried out for fluorescently-labeled high affinity aptamers and the mixture of ten different *S. pyogenes* M-types used for selection ($10^8$ cells). Binding of a fluorescently-labeled randomized oligonucleotide library to the *S. pyogenes* cell mixture served as a negative control. Average gated fluorescence intensity increased linearly with library concentration and was found to reach a maximum of 23% at a library concentration of 150 nM (data not shown). In contrast, all aptamer sequences tested exhibited saturation binding kinetics. The maximum percent gated fluorescence intensity leveled off before or at an aptamer concentration of 50 nM for all sequences tested.

FIGS. 10A-F shows the estimated $K_d$ and predicted secondary structures of the most *S. pyogenes*-selective aptamers. Sequences 20A8 and 20A9 had very high affinities for GAS (respective $K_d$ values of 4±1 nM and 9±1 nM), but are less desirable than other sequences due to their high cross-reactivity with Group B *Streptococcus* and *Enterococcus* cells (FIG. 6).

Figure 11:
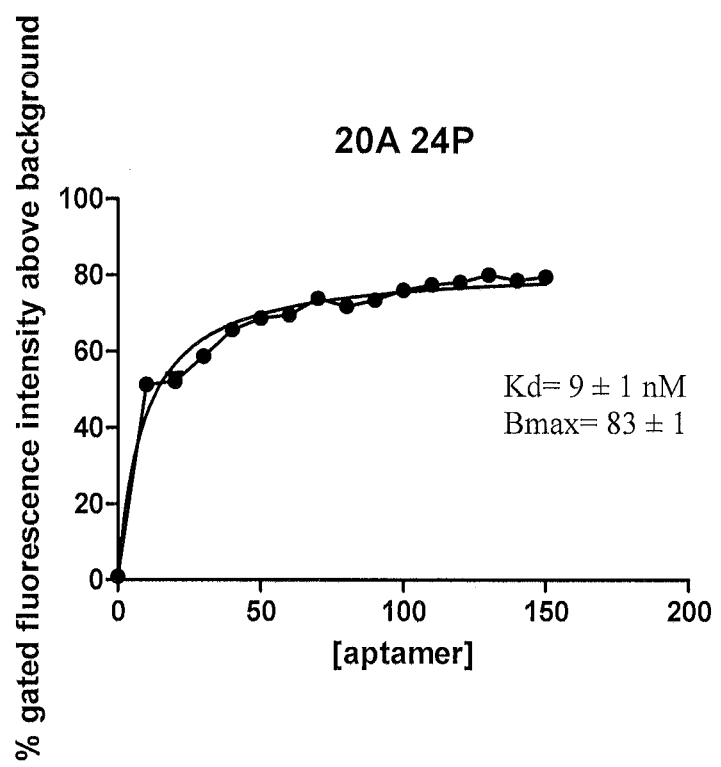
FIG. 11 is a graph showing a binding saturation curve of aptamer 20A24P to the target mixture of S. pyogenes cells.

A non-linear regression fit binding saturation curve for sequence 20A24P is shown as an example in FIG. 11. A mixture containing a total of $10^8$ cells, consisting of $10^7$ cells of each of the 10 target M-types, was incubated with varying concentrations of 20A24P. Flow cytometry was carried out as previously described, except that cells were not washed after incubation, and library binding was not subtracted from the average gated fluorescence values.

Sequences 20A24P, 20A9P, 15A3P had the highest affinities and selectivities for the target cell mixture, since all displayed $K_d$ values below or equal to 10 nM (9.1±0.6 nM for 20A9P; 9.1±0.8 nM for 20A24P; and 9.6±10.3 nM for 15A3P).

In one embodiment, the method of the present invention can be used to select aptamers which may be specific to solely one particular strain of *S. pyogenes*. In one embodiment, the aptamer is specific to *S. pyogenes* M11. A modified cell-SELEX method was employed to generate *S. pyogenes* M-type specific aptamer sequences. The modifications included increasing the starting library diversity and introducing a counterselection step using *S. bovis* cells to remove non-*S. pyogenes* specific sequences. Loss of potential sequences was minimized at each step by increasing incubation time, volume, and mixing of cells and DNA, and by using denaturing gel purification rather than heat denaturation to separate the single-stranded DNA. Typically, many rounds (13-20) of SELEX are required to generate high affinity sequences. The method of the present invention substantially decreases the length of the selection process (for example, 8 rounds of SELEX).

A mixture containing an equal number of cells from each of ten *S. pyogenes* M-types was used as a target (Tyrrell et al., 2002). For SELEX D, a library containing approximately $10^{16}$ unique sequences was used. For SELEX E, a separate library was PCR-amplified and the reverse strand was gel purified, leaving three to four copies of about $10^{14}$ unique sequences. Eight rounds of SELEX D and eight rounds of SELEX E were conducted. The amount of DNA used in each round of selection was maintained at 1 μmole until later rounds (5-8) to minimize loss of potentially desirable aptamer sequences.

Figure 12:
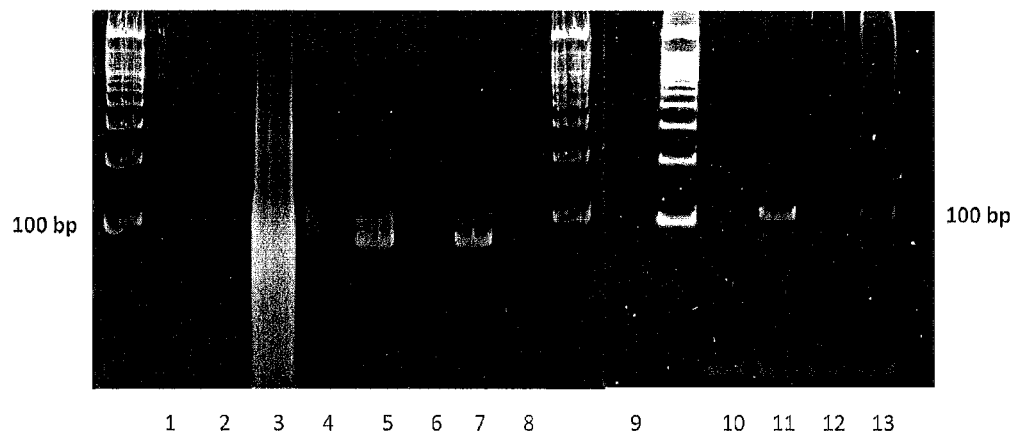
FIG. 12 is a photograph of a polyacrylamide gel (denaturing PAGE) of fractions collected and amplified after round 1 of SELEX D.

Fractions representing the incubation supernatant ("$S_0$"), washes ("W"), heat eluted aptamers ("CA"), and cell-bound aptamers ("Cells") were collected and amplified following incubation. In SELEX D, the majority of the DNA was retained in the supernatant fraction (FIG. 12, Lane 3). A substantial amount of DNA stuck to the cells even after the second wash (Lane 7). The number of washes was increased to three at which point no more DNA came off the cells (Lane 9). The aptamers were heat eluted from the cells at high temperature in low salt (Lane 11), Cells pellets were resuspended and any aptamer sequences which remained bound after elution were amplified (Lane 13). A negative control consisting of cells without added DNA library was run concurrently (Lanes 2, 4, 6, 8, 10, 12). There are several key differences between the first round gels of SELEX E and SELEX D. During SELEX E, most of the DNA was retained in the supernatant, but the total amount of DNA amplified was lower than the supernatant of SELEX D. DNA was still released from the cells after three washes in SELEX E, but not SELEX D.

Figure 13:
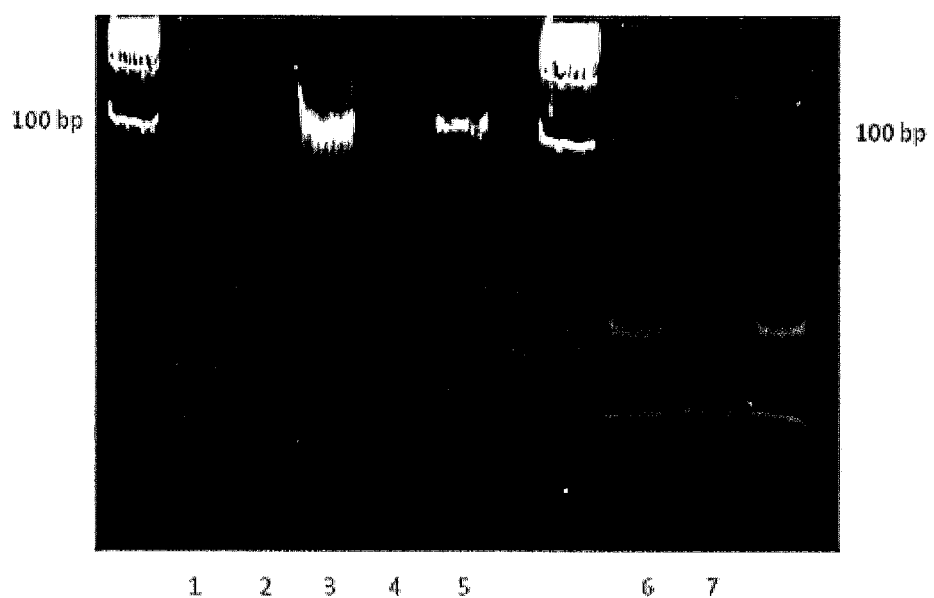
FIG. 13 is a polyacrylamide gel (native PAGE) showing supernatant and wash fractions collected and amplified after round 3 (counterselection) of SELEX D and E. Aptamer pools 2D and 2E were incubated with 109 S. bovis cells. Following incubation, the cells were centrifuged to remove supernatant ($S_O$) and washed to remove DNA sequences that are non-specifically or weakly bound (W1, W2, W3), A negative control was carried out in which cells were incubated (neg$S_O$) and washed negW1, negW2, negW3) in the absence of DNA library. The fractions were PCR amplified and analysed via 7.5% native PAGE. Unlabeled lanes on the gel contain the DNA ladder (100-2072 bp) and lane 1 contains the PCR negative control, Only the $S_O$ and W1 fractions contained DNA, hence they are the only ones shown.

A round of counterselection (designated as SELEX 3D and 3E) was performed after two rounds of SELEX D and E against the *S. pyogenes* mixture. For counterselection, *S. bovis* was used as a target to remove non-*S. pyogenes* specific sequences from the aptamer pools. The entire aptamer pools D and E (1 μmole) were each incubated with $10^9$ *S. bovis* cells under the same conditions as during SELEX. Following incubation, the supernatant and wash fractions were retained and amplified (FIG. 13). The cells were washed three times but DNA was amplified from only the supernatant fractions (Lanes 3, 5) and the first wash fractions (Lanes 6, 7). The majority of the DNA remained in the supernatant fractions. Following PCR, supernatant and wash fractions were pooled, concentrated via ethanol precipitation, and resuspended for use in the next round of SELEX D and E (round 4).

After each round of selection, the single-stranded aptamer pools were assessed for binding affinity and selectivity to the target *S. pyogenes* cell mixture using flow cytometry. The CA fractions and cell fractions obtained after each round of selection were pooled and then fluorescently-labeled and used in flow cytometric assays to assess aptamer pool affinity for the *S. pyogenes* mixture as a whole. A fluorescently-labeled randomized oligonucleotide library was run during each experiment as a control to assess non-specific DNA adhesion to the cells.

Figure 14:
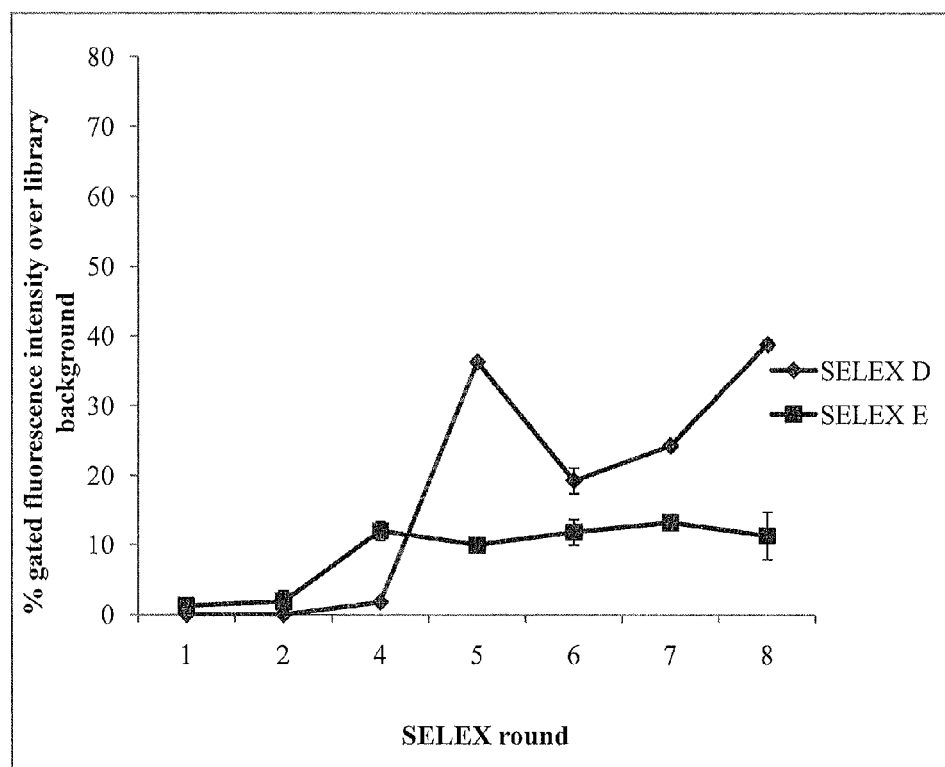
FIG. 14 is a graph showing the change in percent gated fluorescence intensity of S. pyogenes cells incubated with fluorescently-labeled aptamer pools after successive SELEX D and E rounds.

Flow cytometric analyses of incubation mixtures containing fluorescently-labeled aptamer pools from SELEX D and the target cells showed that with increasing rounds of selection, the percent of cells with fluorescence above library background increased to a maximum average of 39% at round 8 for SELEX D aptamer pools and 13% at round 7 for SELEX E (FIG. 14). Controls carried out using fluorescent aptamer pools alone and buffer with BSA and tRNA alone did not yield any increase in gated fluorescence above background levels (data not shown). Without being bound by theory, the increase in the number of fluorescent cells was thus due to the increased binding of the fluorescent aptamers to the target cells. For SELEX D, aptamer pool binding did not start to increase above background until round 4, whereas for SELEX E, the increase was sooner, after round 1. However, for SELEX E, binding did not increase significantly after counterselection (round 3), remaining at a similar level for rounds 4-8. For SELEX D, binding steadily increased after counterselection, decreasing in round 6 only to recover again in rounds 7 and 8.

Upon confirmation that aptamer pool binding was increasing with SELEX rounds, the SELEX D and E aptamer pools were cloned and sequenced after the $8^{th}$ rounds. These pools displayed the highest affinity of later rounds for the target cells when screened via flow cytometry (FIG. 14). Fifty-one sequences from the aptamer pools were obtained, including twenty-five for SELEX D and twenty-six for SELEX E. Heat eluted (CA) and cell-bound (Cells) fractions from round 8 were cloned separately. Secondary structures were predicted using Oligoanalyzer™ 3.1 (Integrated DNA technologies) for all the sequences. All sequences were analyzed both with and without primers. Repetitive sequences or sequences with repetitive structural motifs, sequences with complex secondary structures, hairpin structures similar to hemag1P, and sequences with free energies of formation below −7 kcal/mole were all subjected to further screening. Table 4 summarizes the sequences chosen for screening.

TABLE 4

Screened SELEX D and E aptamer pool sequences with and without primers

| Name | Sequence |
|---|---|
| D CA cells 6 | 5'-GACGGGCGAGGAGGGGACCTCAAGTGGGTTCGGTG-3' (SEQ ID NO: 16) |
| D CA cells 6P | 5'-<u>AGCAGCACAGAGGTCAGATG</u>GACGGGCGAGGAGGGGACCTCAAGTGGGTTCGGTG<u>CCTATGCTGCTACCGTGAA</u>-3' (SEQ ID NO: 17) |
| D CA 17 | 5'FAM/GACGGTTCTGAGGGAGGGGACCTCAAGTGGGTTCGGTG-3' (SEQ ID NO: 18) |
| D CA 17P | 5'-<u>AGCAGCACAGAGGTCAGATG</u>GACGGTTCTGAGGGAGGGGACCTCAAGTGGGTTCGGTG<u>CCTATGCGTGCTACCGTGAA</u>-3' (SEQ ID NO: 19) |
| D cells 1 | 5'-CCCCACGAATCGGTACTCTGGTCCTCTATTTCTCCTCCCC-3' (SEQ ID NO: 20) |
| D cells 1P | 5'-<u>AGCAGCACAGAGGTCAGATG</u>CCCCACGAATCGGTACTCTGGTCCTCTATTTCTCCTCCCC<u>CCTATGCGTGCTACCGTGAA</u>-3' (SEQ ID NO: 21) |
| D cells 9 | 5'FAM/GGGGAGGAGAAAAAGAGGACCAGAGTAACGATTCGTGGGG-3' (SEQ ID NO: 22) |
| D cells 9P | 5'-<u>TTCACGGTAGCACGCATAGG</u>GGGGAGGAGAAAAAGAGGACCAGAGTAACGATTCGTGGGG<u>CATCTGACCTCTGTGCTGCT</u>-3' (SEQ ID NO: 23) |
| D cells 20 | 5'-GGGGAGGAGAAATAGAGGACCAGAGTAACGATTCGTGGGG-3' (SEQ ID NO: 24) |
| D cells 20P | 5'-<u>TTCACGGTAGCACGCATAGG</u>GGGGAGGAGAAATAGAGGACCAGAGTAACGATTCGTGGGG<u>CATCTGACCTCTGTGCTGCT</u>-3' (SEQ ID NO: 25) |
| E CA 4 | 5'-GGCACCAAGCAAAAATCGTAATGTTGGTGGTACACTTCGG-3' (SEQ ID NO: 26) |
| E CA 4P | 5'-<u>TTCACGGTAGCACGCATAGG</u>GGCACCAAGCAAAAATCGTAATGTTGGTGGTACACTTCGG<u>CATCTGACCTCTGTGCTGCT</u>-3' (SEQ ID NO: 27) |
| E CA 9P | 5'-<u>AGCAGCACAGAGGTCAGATG</u>CCTCACGAACGGTACTCTGGTCCTCTATTTCTCCTCCCC<u>CCTATGCGTGCTACCGTGAA</u>-3' (SEQ ID NO: 28) |
| E CA 20 | 5'-CACACACGGAACCCCGACAACATACATACGGTGAGGGTGG-3' (SEQ ID NO: 29) |
| E CA 20P | 5'-<u>TTCACGGTAGCACGCATAGG</u>CACACACGGAACCCCGACAACATACATACGGTGAGGGTGG<u>CATCTGACCTCTGTGCTGCT</u>-3' (SEQ ID NO: 30) |
| E cells 1 | 5'-GGGGAGGAGAAAAGAGGACCAGAGTAACGATTCGTGGGG-3' (SEQ ID NO: 31) |
| E cells 1P | 5'-<u>TTCACGGTAGCACGCATAGG</u>GGGGAGGAGAAAAGAGGACCAGAGTAACGATTCGTGGGG<u>CATCTGACCTCTGTGCTGCT</u>-3' (SEQ ID NO: 32) |

There was a high amount of repetition within the SELEX D and E aptamer pools, and many sequences contained high GC content, indicative of potential formation of secondary structures. Many of the secondary structures formed were similar even if the sequences were similar, but not identical. Two sequences, D cells 1 and D cells 9, were highly repeated within and between the D and E aptamer pools (Table 4). D cells 1 was repeated thirteen times in the SELEX D pool, and seven times in the SELEX E pool. D cells 9 was repeated twelve times in the SELEX D pool and fourteen times in the SELEX E pool. The sequences D cells 1 and D cells 9 formed similar secondary structures both with and without primers. Other sequences sharing these secondary structural motifs were often similar yet not identical, for example, 8D cells 9 and 8D cells 20 (Table 4). Several other sequences and structural motifs were repeated both within and between aptamer pools (data not shown).

Figure 15:
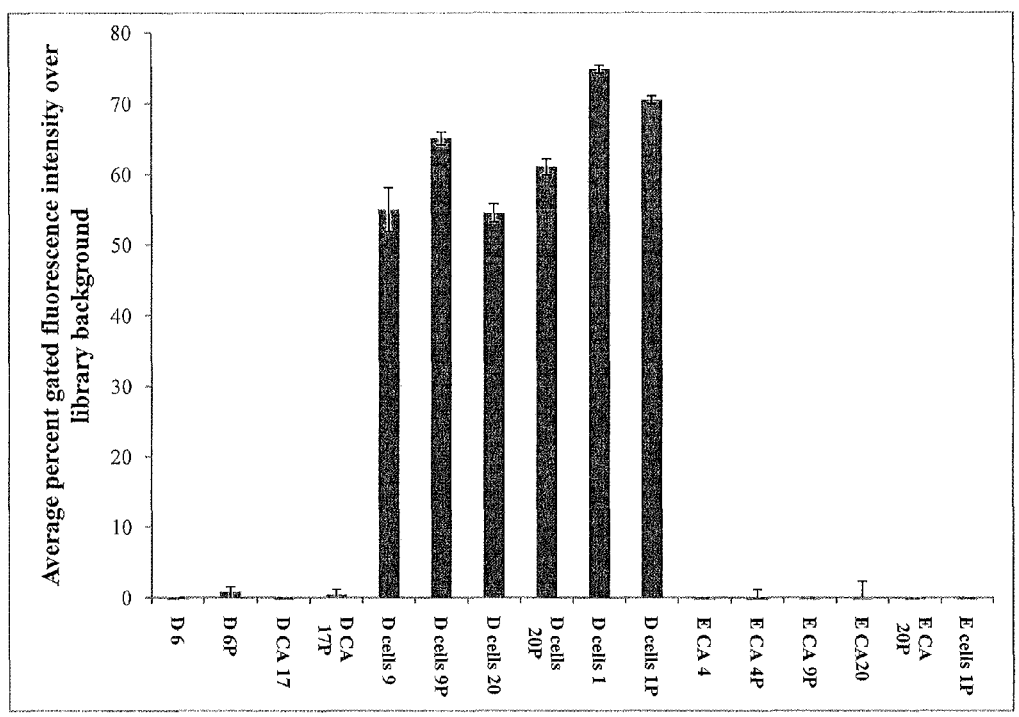
FIG. 15 is a graph showing screening of sequences from SELEX D and E aptamer pools (200 pmole of aptamer and $10^8$ total cells).

Individual aptamer sequences were fluorescently-labeled, and each aptamer was incubated with the target mixture of ten S. pyogenes M-types used for selection. The cells were washed and subjected to flow cytometry without elution of the aptamers bound to the cell surface. As predicted from the aptamer pool binding profiles in FIG. 14, SELEX D seemed to produce more high affinity aptamer sequences than SELEX E. None of the tested SELEX E sequences showed significant binding to the *S. pyogenes* mixture (FIG. 15). Neither did any of the SELEX D sequences found in the CA fraction (D6, D6P, DCA17, DCA17P). The aptamer sequences unique to the SELEX D cells fractions appeared to have the highest affinity for the cell mixture (D cells 9, 9P, 20, 20P, 1, 1P). All six sequences unique to the SELEX D cell fraction pool had greater than 50% average gated fluorescence intensity above a randomized library control. Sequences D cells 1, D cells 1P (with primers), were the highest binders with gated fluorescence above background values of 75% and 71%, respectively. The second highest binding sequence was D cells 9P with a gated fluorescence above background of 65%. The D cells 9, 20, and 20P had percent gated fluorescence intensities above library of 55%, 55%, and 61% respectively.

Sequences D cells 1, 9, and 20 have very similar secondary structures. The sequence D cells 1 has only four base-pairing interactions in its predicted secondary structure, whereas D cells 9 and 20 have five. In the presence of primers, D cells 9 and 20 form identical secondary structures. D cells 1 form a different secondary structure when primers are included. The small differences in secondary structure of D cells 1 and 1P from the other sequences seems to account for their slightly higher binding to the target cell mixture over the other sequences (FIG. 15). The similarity of the predicted secondary structures of D cells 9 and 20 is hardly surprising due to their sequence similarity (Table 4). The affinity of these three aptamers for the *S. pyogenes* mixture changes minimally upon inclusion or exclusion of primers in the sequence; hence, the target binding site must be in a central region of the sequence.

The binding of aptamers to specific M-types was determined. Individual aptamer sequences were screened via flow cytometry against each M-type separately. Sequences E CA 20, E CA 20P, and E cells 1P were chosen from the SELEX E pool. Since D cells 9 and D cells 20 are virtually identical sequences, D cells 9 and D cells 9P were chosen for further screening along with D cells 1 and 1P from the SELEX D pool. A fluorescently-labeled randomized oligonucleotide library was used as a negative control.

Figure 16:
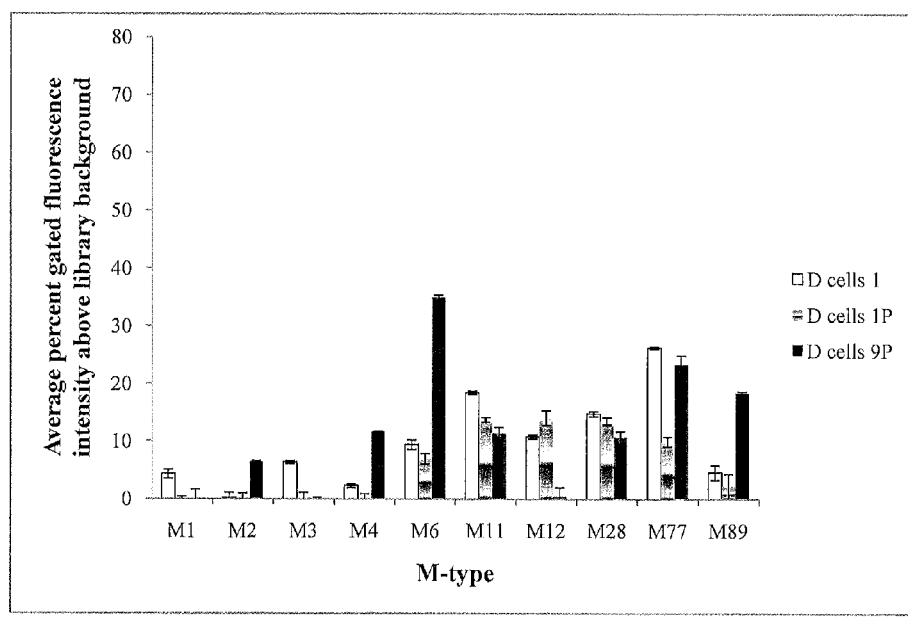
FIG. 16 is a graph showing binding of aptamer sequences with high affinity to the target cell mixture to separate S. pyogenes M-types (200 pmole of aptamer and $10^8$ total cells).
Figure 17:
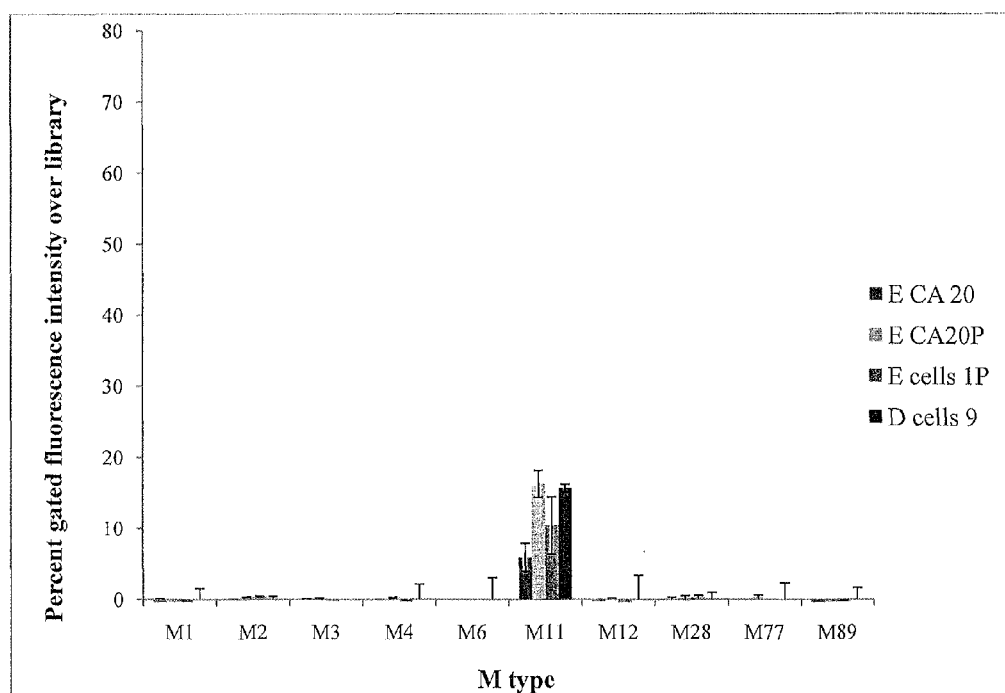
FIG. 17 is a graph showing selective binding of aptamer sequences from SELEX D and E to S. pyogenes M11 cells (200 pmole of aptamer and $10^8$ total cells).

The selection resulted in aptamer pools containing a mixture of sequences with different affinities for different targets. The affinity of a given sequence for the *S. pyogenes* mixture did not always mirror its affinity for each M-type. Many sequences with high affinity for the cell mixture had broad spectrum affinity for most M-types, with demonstrable binding to all M-types. For example, D cells 1 bound to all M-types except M2 (FIG. 16). Sequences with low affinity to the cell mixture were specific for M11 cells. All exhibit binding to M11 cells only with percent gated fluorescence intensities below 20%. The sequence D cells 9 appears to be specific for M11 cells, binding only to M11 cells with a percent gated fluorescence intensity above library background of 16% (FIG. 17). This result was unexpected since D cells 9 has a relatively high affinity for the overall mixture (55% gated fluorescence intensity above background in FIG. 15), but demonstrates only a medium range affinity for M11 cells and no affinity for other M-types. The addition of primers to the sequence D cells 9 seems to negate its M11 selectivity, also resulting in higher affinity for the *S. pyogenes* mixture (65% gated fluorescence intensity above library background in FIG. 15). The sequence D cells 9P has broad-spectrum affinity for all M-types except M1 and M3 (FIG. 17).

Figure 18:
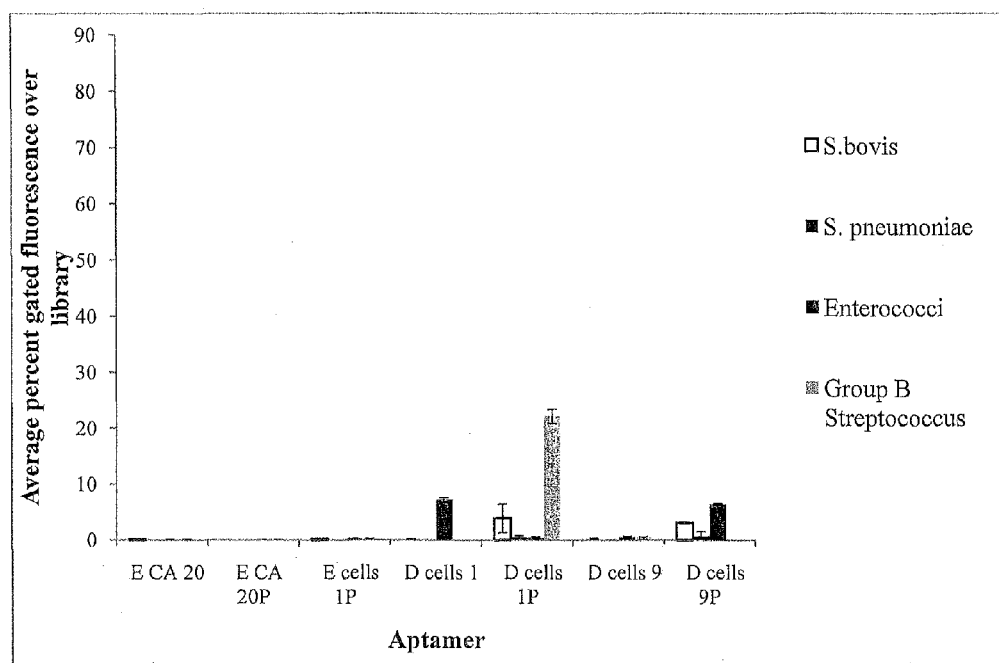
FIG. 18 is a graph showing screening of M11-specific GAS aptamers against non-target cells (200 pmole of aptamer and $10^8$ total cells).
Figure 19A:
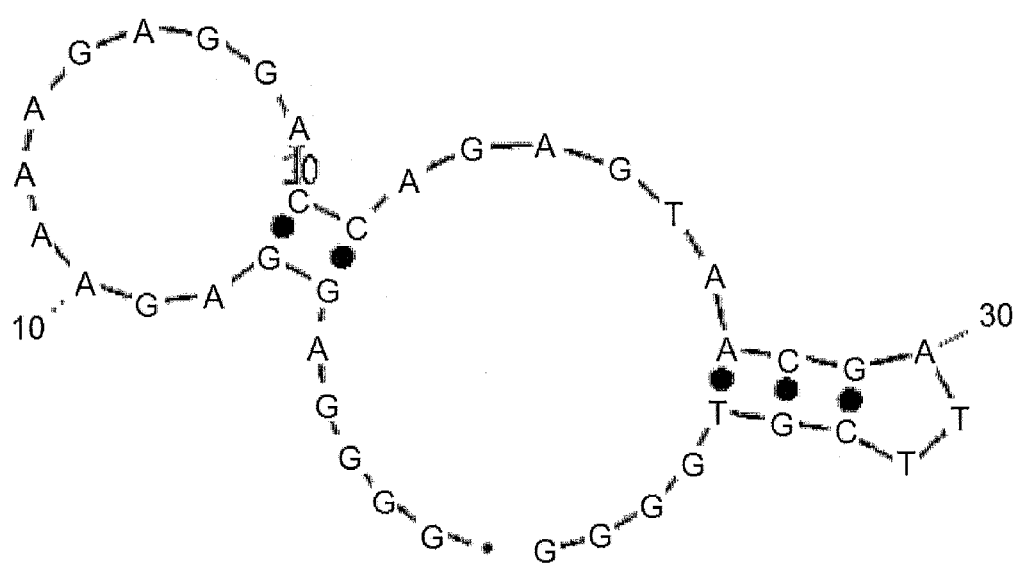
Figure 19B:
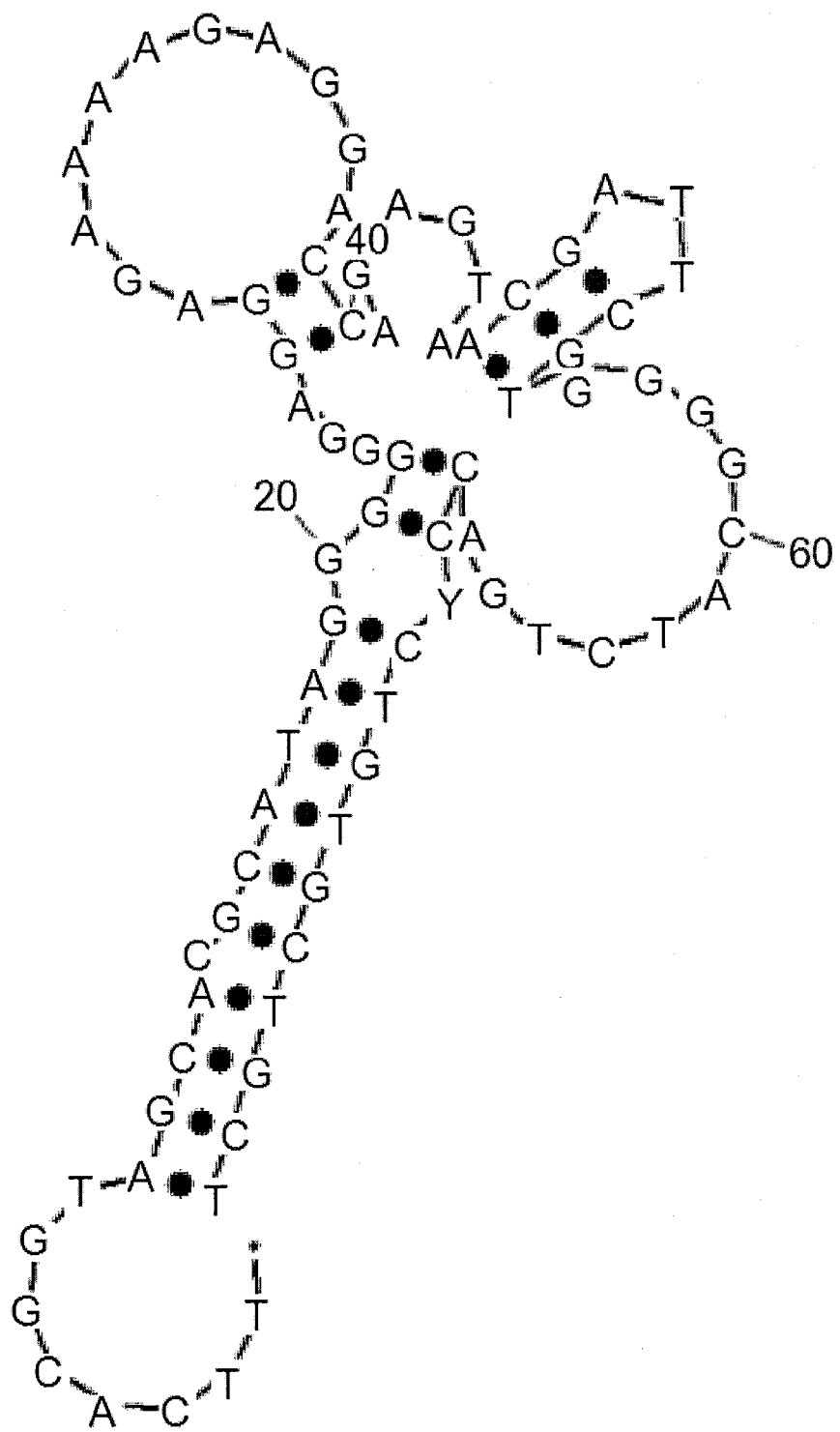
Figure 19C:
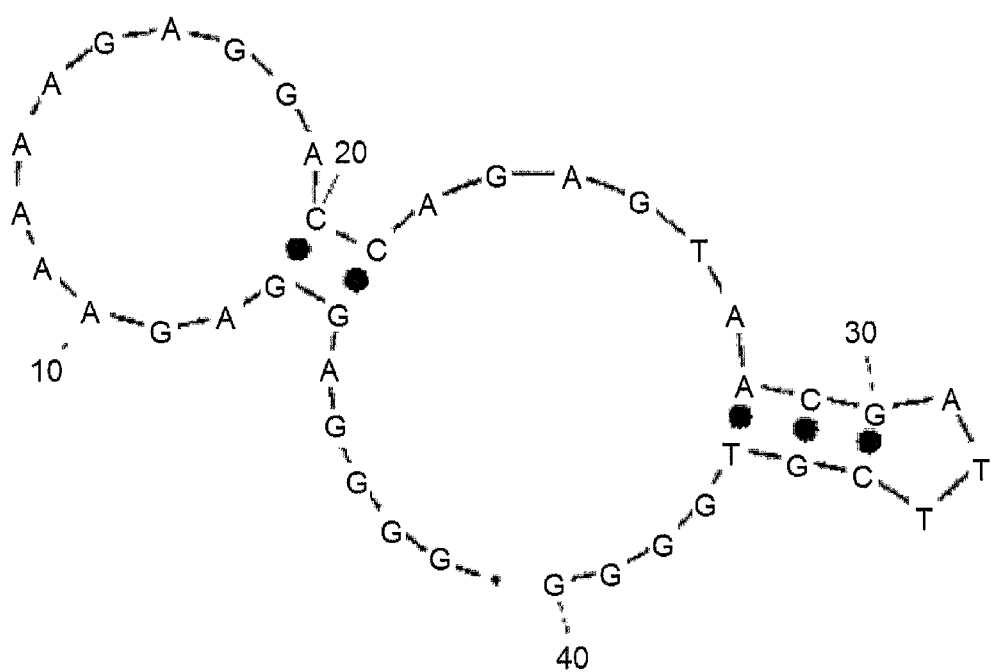
Figure 19E:
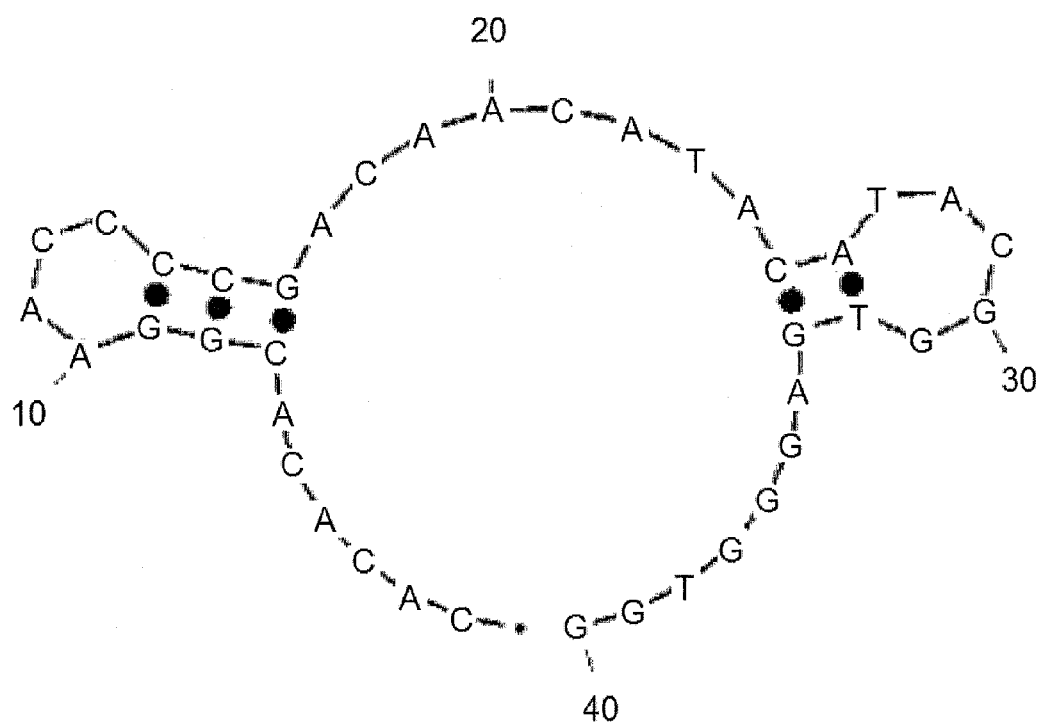
Figure 19F:
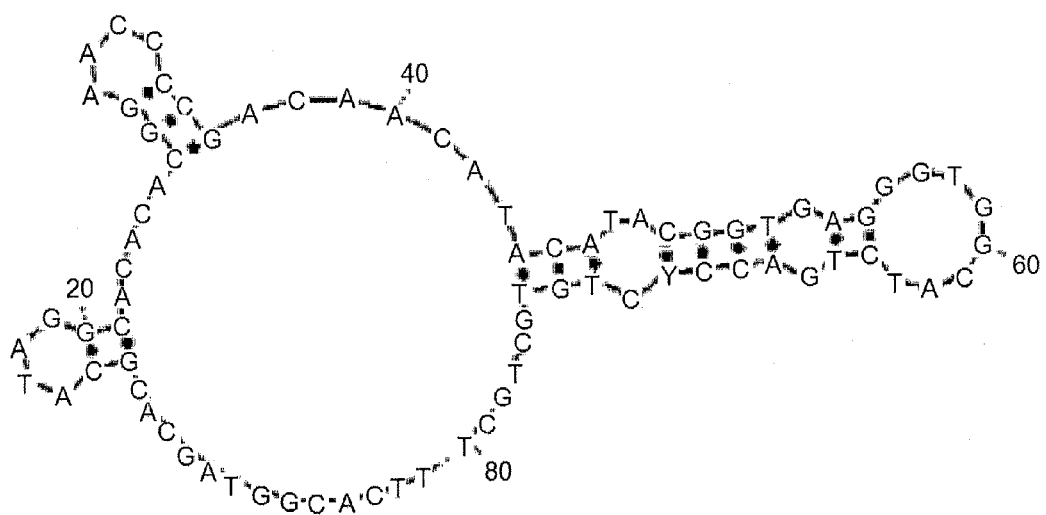

Fluorescently-labeled M11 specific aptamer sequences were tested against a variety of other bacteria including non-pathogenic *S. bovis*, *S. pneumonia* and *S. agalactiae* (GBS), and *Enterococcus* sp (FIG. 18). For the *S. pneumoniae*, *S. agalactiae*, and *Enterococcus* isolates, mixtures were prepared containing an equal number of cells from multiple isolates, as were the *S. pyogenes* mixtures used for selection. The sequence D cells 1P showed significant binding to GBS, with an average percent gated fluorescence intensity above background of over 20%. Sequence D cells 9P showed a small amount of binding to the Enterococci mixture (6 percent gated fluorescence intensity above background). Sequence D cells 9 appears to be very specific for *S. pyogenes* since it did not bind to any of the other cell types tested.

FIGS. 19A-F shows the predicted structures of aptamer sequences with high affinity and selectivity for *S. pyogenes* M11. All structures were predicted using Oligoanalyzer™ 3.1, with conditions set to 21° C., 100 mM NaCl, and 1 mM $MgCl_2$.

Figure 20:
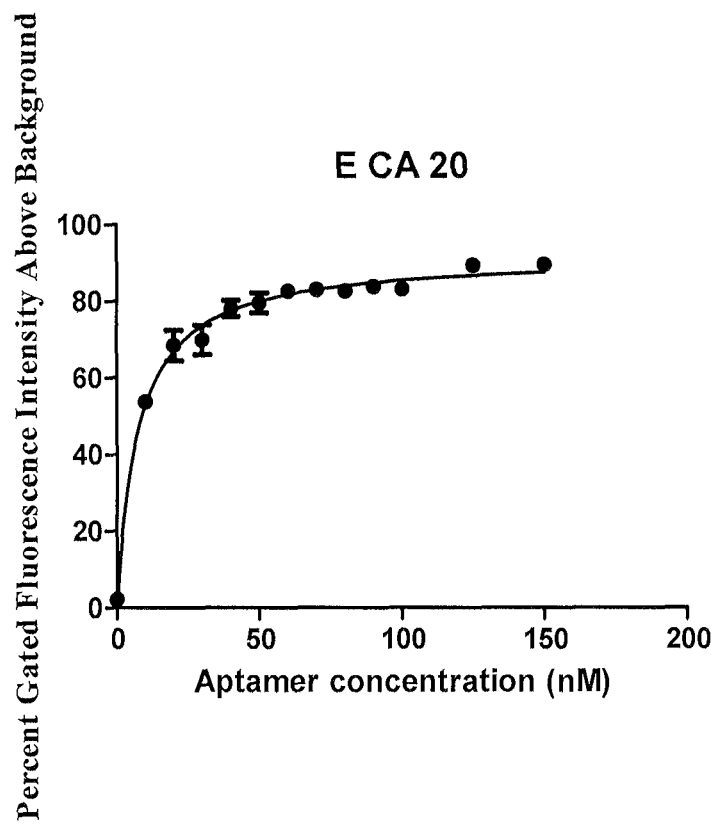
FIG. 20 is a graph showing the binding affinity saturation curve of M11-selective aptamer E CA 20 with M11 cells.

Binding saturation curves were generated for the M11 specific aptamer sequences and *S. pyogenes* M11 cells. The results of flow cytometric analysis of fluorescently-labeled aptamer E CA 20 and *S. pyogenes* M11 ($10^9$ cells) is shown as an example in FIG. 20. Similar curves were generated for the other sequences (data not shown). Aptamer concentrations in the incubation supernatant from 0 to 150 nM were tested, with the amount of aptamer binding found to level off at less than 70 nM for all sequences. Binding of a fluorescently-labeled randomized oligonucleotide library to the *S. pyogenes* cell mixture was also examined over a concentration range of 0 to 150 nM (data not shown). The average gated fluorescence intensity increased linearly with library concentration and was found to reach a maximum of 57% at a library concentration of 150 nM. However, for all aptamer sequences tested, maximum percent gated fluorescence intensity above background followed an exponential curve, reaching a maximum and leveling off before or at an aptamer concentration of 70 nM. All sequences except D cells 9P had curves that leveled off at or below a concentration of 40 nM.

The binding dissociation constant ($K_d$) of each aptamer was determined based on the fit of a non-linear regression curve (Table 5).

TABLE 5

Binding dissociation constant ($K_d$, nM) and theoretical maximum binding ($B_{max}$) of high affinity SELEX D aptamer sequences for M11 *S. pyogenes* cells

| | | |
|---|---|---|
| D cells 9 | 71 | 23 |
| D cells 9P | 44 | 8 |
| E CA 20 | 7 | 1 |
| E CA 20P | 12 | 1 |
| E cells 1P | 20 | 3 |

Sequences E CA 20 and E CA 20P had the highest affinities for M11 cells, since both exhibited $K_d$ values in the low nanomolar range ($K_d$=7±1 nM for E CA 20; 12±1 nM for E CA 20P). Sequence D cells 9 had the lowest affinity for M11 cells with a $K_d$ of 71±23 nM. The maximum percent gated fluorescence intensity measured for each sequence is as follows: 1) D cells 9: 77±4% at 150 nM; 2) D cells 9P: 79±4% at 150 nM; 3) E CA 20: 89±0.3% at 125 nM; 4) E CA 20P: 87±1% at 125 nM; and 5) E cells 1P: 79±1% at 125 nM. Since the percent gated fluorescence intensity value increases with the number of cells bound to an aptamer and the number of target molecules (and hence aptamers) bound per cell, it appears that aptamer sequences D cells 9, D cells 9P and E cells 1P bind to slightly fewer cells and/or fewer target molecules per cell than E CA 20 and E CA 20P.

Many of the aptamers obtained were thus species but not strain specific. Sequence D cells 9P was specific for *S. pyogenes* with a predicted $K_d$ of 4±1 nM. The sequence D cells 9 also had high affinity and selectivity for *S. pyogenes* with a predicted $K_d$ of 17±3 nM. While most of the aptamers generated could bind to all M-types, these sequences were found to bind specifically to one M-type, M11. Several additional sequences, 8E CA 20, 8E CA 20P and 8E cells 1P, also bound specifically to M11 with high affinities (low nanomolar $K_d$). The highest affinity sequence isolated is E CA 20, with a predicted $K_d$ of 7±1 nM.

The aptamers may be in the form of a kit which includes all necessary aptamers and reagents for testing a sample. In one embodiment, the invention comprises a kit for detecting the presence of *S. pyogenes* comprising an aptamer or a panel of aptamers, reagents for detecting the binding of the aptamer or panel of aptamers to *S. pyogenes*, and one or more supports.

Aptamers of the present invention may be affixed to a support to develop an aptamer array for high-throughput M-typing of clinical isolates. Suitable supports include, but are not limited to, a glass or silicon surface, an electronic sensor array (e.g., a silicon chip), or a silicon pin array. A direct assay or a sandwich format assay may be used to capture whole cells or the extracted M-proteins out of solution. The direct assay involves using the array to capture GAS cells of a specific M-type out of solution, and then fixing and counting the number of captured cells. The array may be visualized using for example, a light microscope. In the sandwich assay, the captured cells or protein are visualized with a second fluorescently-labeled aptamer against the M protein or a fluorescently-labeled antibody recognizing the non-variable M-protein C-terminus or a GAS cell wall component common to all M-types, such as the group A carbohydrate or peptidoglycan. The array is analyzed using for example, a fluorescent microscope or a microarray reader. Such arrays are similar in principle to those described by Kirby et al. (2004) and Cho et al. (2006).

The aptamer sequences from the GAS mixture aptamer pool may be attached to the same slide or chip to yield a different aptamer "fingerprint" for each isolate. The "fingerprint" would result from each aptamer in the pool having different affinity and selectivity for the surface molecules on each M-type. The aptamers may also be arranged in an array where each pin is covered in aptamers specific to one M-type. GAS isolates of unknown M-type may be screened using the pin array. The bacteria are retained only on the pins covered by the aptamers specific to their M-type. The array may then be used to stamp agar plates and the specific pattern of bacterial growth on the plates used to determine M-type.

Exemplary embodiments of the present invention are described in the following Example, which is set forth to aid in the understanding of the invention, and should not be construed to limit in any way the scope of the invention as defined in the claims which follow thereafter.

Example 1

Bacterial Strains and Culture Medium

*Streptococcus pyogenes* clinical isolates corresponding to M types M1, M2, M3, M4, M5, M6, M11, M12, M28, M41, M49, M59, M75, M77, M82, M83, M89, M91, M92, and M114 were obtained from the National Centre for *Streptococcus* (Provincial Laboratory, Edmonton, AB). *S. pyogenes* isolates were streaked out on 5% defibrinated sheep's blood agar (Teknova, Hollister, Calif.) and single colonies were cultured in Todd-Hewitt Broth (Oxoid, Nepean, ON). *Streptococcus bovis* and *Escherichia coli* were obtained from the American Type Culture Collection (ATCC) and were cultured in Brain Heart Infusion (BHT) (Teknova) and Luria-Bertani (LB) media (BD Difco, Sparks, Md.), respectively. *Streptococcus pneumoniae* (serotypes 4, 6B, 9V, 14, 18C, 19F, 23F, 19A, 5, and 6A), *Enterococcus* sp. (*E. sacchrolyticus, E. raffinsous, E. pseudoarium, E. mundtii, E. malodoratus, E. hirap, E. gallinarium, E. faecium, E. faecalis, E. durans, E. cecorum, E. casseliflavus, E. avium*) and Group B *Streptococcus* strains (975R547 IV, JM9 VIII, 7271 VII, 975R390 VI, 965R4001a, 975R384 V, 12351 IV, 965R155 Ia, 975R938 II, 975R27 Ib, 975R331 IV, 955R2028 IV, 975R591 III, 975R138 II, 975R570 Ib, 975R104 VII, 9842 VI, 975R594 III) were also obtained from the National Centre for *Streptococcus*. *S. pneumoniae* and *Enterococcus* sp. were on 5% defibrinated sheep's blood agar and streaked out cultured in BHI broth and GBS isolates were cultured in TH broth. All bacteria were cultured overnight in aerobic conditions at 37° C., and all liquid cultures were shaken at 200 rpm. *E. coli* DH5α-T1$^R$ cells (Invitrogen, Carlsbad, Calif.) were used for all transformations.

Example 2

DNA Library i. Selection of Aptamers Specific to a Plurality of Strains of *S. pyogenes*

An 80-nt oligonucleotide single-stranded DNA library consisting of a 40 nt randomized region flanked on both sides by 20-nt primer regions was used. The initial ssDNA library and the primers used to amplify it were obtained from Integrated DNA Technologies (Coralville, Iowa). DNA library or aptamer pools were rendered single-stranded via heat denaturation at 94° C. for 10 min and subsequent cooling at 0° C. for 5 min.

ii. Selection of Aptamers Specific to *S. pyogenes* M11

Two separate 80-nt oligonucleotide single-stranded DNA libraries consisting of a 40-nt randomized region flanked on both sides by 20-nt primer regions were used. The initial ssDNA library and the primers used to amplify it were obtained from Integrated DNA Technologies (Coralville, Iowa). SELEX set D was carried out using the single-stranded library containing a maximum of $10^{16}$ different sequences without amplification (as it arrived from IDT), while SELEX E was carried out using a second, PCR amplified library. The entire second library was amplified for 3 cycles using the standard PCR conditions already described, and thus contained approximately 3-4 copies of the reverse strand of each of the original sequences. The total number of unique starting sequences used for SELEX E was about $10^{14}$. Prior to incubation with target cells single-stranded oligonucleotides were treated via heat denaturation at 94° C. for 5 min and subsequent cooling at 0° C. for 10 min.

Example 3

PCR Amplification and Gel Electrophoresis i. Selection of Aptamers Specific to a Plurality of Strains of *S. pyogenes*

The primers used to amplify the ssDNA library and subsequent aptamer pools have the following sequences:

```
                                      (SEQ ID NO: 33)
Forward:  5'-AGCAGCACAGAGGTCAGATG-3'

(SEQ ID NO: 34)
Reverse:  5'-TTCACGGTAGCACGCATAGG-3'
```

The PCR conditions for amplification of the DNA aptamer pools during SELEX were similar as described by Hamula et al. (2008).

ii. Selection of Aptamers Specific to *S. pyogenes* M11

The forward primer contains a 5' polyA overlap of 20 adenine residues joined to the remaining primer sequence via a triethylene glycol spacer (IDT Spacer 9). The primers used to amplify the ssDNA library and subsequent aptamer pools have the following sequences:

```
Forward:
                                        (SEQ ID NO: 35)
5'-A20/5Sp9/AGCAGCACAGAGGTCAGATG-3'

(SEQ ID NO: 36)
5'-AGCAGCACAGAGGTCAGATG-3'

Reverse:
                                        (SEQ ID NO: 37)
5'-TTCACGGTAGCACGCATAGG-3'
```

The PCR conditions for amplification of the DNA aptamer pools during SELEX were optimized after each round, in order to choose the highest cycle number at which misamplification products do not form. This cycle number was 3 for round 1, 7 for round 2, 7 for round 3 (counterselection round), 12 for round 4, and 20 for rounds 5-8. The amount of primers and nucleotides were increased compared to previous SELEX PCR conditions, in proportion to the increased amount of DNA being amplified. The standard PCR conditions were used for SELEX D and E: 1×PCR reaction buffer, 2 mM $MgCl_2$, 2.0 µM of each primer, 0.5 mM dNTPs, 1 E.U. of Platinum Taq DNA Polymerase, and 39.5 µL of fraction supernatant (all reagents were from Invitrogen). Thermocycling parameters were 94° C. for 5 min denaturation, followed by up to 20 cycles of denaturation at 94° C. for 30 s, annealing at 57° C. for 30 s, and extension at 72° C. for 20 s. A final extension step of 72° C. for 5 min was carried out following the last cycle (MJ Mini Gradient Thermocycler; Bio-Rad Laboratories, Hercules, Calif.).

After PCR in both i and ii above, the reaction products were separated on 7.5% non-denaturing polyacrylamide gel electrophoresis (PAGE) in 1×TBE buffer (Bio-Rad Protean III) at 60-120 V. The gels were stained with ethidium bromide, and photographed under UV light.

Example 4

Denaturing Gel Electrophoresis and Gel Purification

DNA library or aptamer pools were rendered single-stranded via gel purification on a denaturing gel after amplification. Denaturing PAGE was carried out using 9% gels containing 8 M urea and 25% v/v formamide. After running the gel at 60-120 V and staining with ethidium bromide, the 100 nt forward strand could be distinguished from the 80 nt reverse strand, which was sliced from the gel. A Qiaex II Gel Extraction Kit (Qiagen) was used to purify the reverse strand from the slices. Upon purification single-stranded DNA was stored at −20° C. in 10 mM Tris-HCl pH 8.0.

Example 5

Aptamer Selection i. Selection of Aptamers Specific to a Plurality of Strains of *S. pyogenes*

SELEX was carried out using a procedure modified from Hamula et al. (2008). Single colonies of ten different *S. pyogenes* M-types (M1, M2, M3, M4, M6, M11, M12, M28, M77, and M89) were grown overnight in separate liquid cultures. The cells were then sub-cultured to a second set of tubes (with a 1:100 inoculum to media ratio) and were harvested upon reaching logarithmic phase (minimum $OD_{600}$ of 0.3). Aliquots containing the same number of cells from each culture were combined only once growth was complete. Cell mixtures were centrifuged at 6000×g and 4° C. for 10 minutes to remove media and to remove wash supernatants. The varying SELEX incubation conditions and amounts of reagents per round are summarized in Table 6. The ratio of DNA to cells was kept constant. SELEX A was initiated with randomized ssDNA library (2 nmole initial round), and 100 pmole of aptamer pool were used as inputs in subsequent rounds. A total of $10^8$ cells, containing an equal number of cells of each M-type ($10^7$), were used for each round of selection. An excess of tRNA and BSA (Invitrogen) were added to the incubation buffer (20-fold molar excess of each in the initial round, up to a maximum 400-fold molar excess in rounds 20) and 0.05% w/v BSA was added to the wash buffer. The use of increasing amounts of BSA/tRNA increases the competition between the desired target (cells) and non-targets (BSA molecules) for aptamer molecules. The tRNA is present to compete with the aptamer sequences for target binding sites. Twenty sets of SELEX A were performed.

Figure 4:
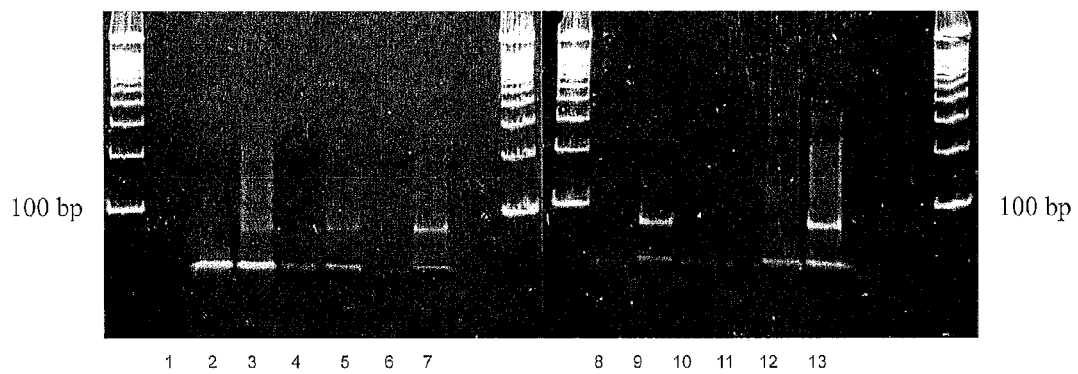
FIG. 4 is a photograph of a polyacrylamide gel of PCR-amplified oligonucleotide fractions after the first round of SELEX A/B. The far left, the far right, and the two central lanes on the gel contain the DNA ladder (100-2072 bp) and Lane 1 contains the PCR negative control. Lanes 2 and 3 contain the incubation supernatant from the positive SELEX experiment ($S_0$, Lane 3) and the negative control (neg $S_0$, Lane 2). Lanes 5, 7, 9 and 11 contain the wash fractions from the positive SELEX experiments (W1, W2, W3, and W4 respectively), while Lanes 4, 6, 8, and 10 contain the wash fractions from the negative control (neg W1-neg W4). Lanes 12 and 13 contain the heat-eluted cell-bound aptamer fractions from the positive experimental (Lane 13) and negative control (Lane 12) samples.

Following incubation, the cells were centrifuged to remove the incubation supernatant (So) and repeatedly washed in binding buffer to remove DNA sequences that are non-specifically or weakly bound (W1, W2, W3, W4). The cells were next heated at 94° C., the suspension was centrifuged, and the supernatant was collected containing the heat-eluted cell aptamer fraction (ECA). A SELEX negative control was carried out in which cells were incubated in the absence of DNA library (neg $S_0$), washed (negW1, negW2, negW3, neg W4), and heat-eluted (negECA). The different fractions collected during SELEX (So, W1-W4, ECA) and the parallel negative control were PCR amplified and analysed via PAGE (FIG. 4).

All washes and incubations were carried out in 1× Binding Buffer (1×BB) (50 mM Tris-HCl (pH 7.4), 5 mM KCl, 100 mM NaCl, 1 mM $MgCl_2$) at room temperature for 45 minutes. An initial incubation volume of 0.5 mL was used for round one, and this was decreased to 0.25 mL for subsequent rounds; 4 washes were carried out for each round of SELEX A until round 8 at which the number of washes was decreased to 3 in order to increase the yield after amplification. To confirm the applicability of the multi-target cell-SELEX method, we also carried out a second SELEX set for 13 rounds, SELEX B.

In SELEX A, conditions were the same as in Hamula et al. (2008) and described herein. In SELEX B, the DNA:cell ratio was altered in favour of increased competition between DNA sequences for target cells. The varying incubation conditions of both SELEX sets are summarized in Table 6. In SELEX B, competition between DNA sequences for a limited number of target cells was steadily increased by altering the DNA:cell ratio. Practically, pellets containing fewer than $10^5$ cells are difficult to handle without losing so the cell number was not decreased beyond this point. In addition, PCR amplification of fewer than 50 pmole of DNA at low cycle numbers resulted in poor CA fraction yields. Both SELEX A and B were initiated with ssDNA library (2 nmole initial round). The aptamer pools used for incubation in SELEX B were decreased from 100 pmole for round 2 to 75 pmole for rounds 3 through 7, and then increased to 100 pmole again for rounds 9 through 11. The final two rounds of SELEX B, rounds 12 and 13, were carried out with 175 pmole of DNA. A total of $10^8$ cells, containing an equal number of cells of each M-type ($10^7$), were used for each round of selection in SELEX A. For SELEX B, the total number of cells was decreased from $10^8$ to $10^5$ over rounds 5 to 8 and maintained at $10^5$ for rounds 9-13. Three washes were carried out for rounds 3-13 of SELEX B; 4 washes were done in rounds 1 and 2. Twenty rounds of SELEX A and thirteen rounds of SELEX B were completed. All other conditions were kept the same between SELEX A and B. The end result is that SELEX B should have higher stringency than SELEX A. Thirteen sets of SELEX B were performed.

TABLE 6

Selection conditions for SELEX A and B against *S. pyogenes*

| | Molar Excess BSA/tRNA | DNA:cell ratio SELEX A | DNA:cell ratio SELEX B |
|---|---|---|---|
| 1 | 20x | 2000 pmole:$10^8$ cells | 2000 pmole:$10^8$ cells |
| 2 | 40x | 100 pmole:$10^8$ cells | 100 pmole:$10^8$ cells |
| 3 | 60x | 100 pmole:$10^8$ cells | 75 pmole:$10^8$ cells |
| 4 | 80x | 100 pmole:$10^8$ cells | 75 pmole:$10^8$ cells |
| 5 | 100x | 100 pmole:$10^8$ cells | 75 pmole:$5 \times 10^7$ cells |
| 6 | 120x | 100 pmole:$10^8$ cells | 75 pmole:$10^7$ cells |
| 7 | 140x | 100 pmole:$10^8$ cells | 75 pmole:$5 \times 10^6$ cells |
| 8 | 160x | 100 pmole:$10^8$ cells | 100 pmole:$10^6$ cells |
| 9 | 180x | 100 pmole:$10^8$ cells | 100 pmole:$10^6$ cells |
| 10 | 200x | 100 pmole:$10^8$ cells | 100 pmole:$5 \times 10^5$ cells |
| 11 | 220x | 100 pmole:$10^8$ cells | 100 pmole:$5 \times 10^5$ cells |
| 12 | 240x | 100 pmole:$10^8$ cells | 125 pmole:$10^5$ cells |
| 13 | 260x | 100 pmole:$10^8$ cells | 125 pmole:$10^5$ cells |
| 14 | 280x | 100 pmole:$10^8$ cells | N/A |
| 15 | 300x | 100 pmole:$10^8$ cells | N/A |
| 16 | 320x | 100 pmole:$10^8$ cells | N/A |
| 17 | 340x | 100 pmole:$10^8$ cells | N/A |
| 18 | 360x | 100 pmole:$10^8$ cells | N/A |
| 19 | 380x | 100 pmole:$10^8$ cells | N/A |
| 20 | 400x | 100 pmole:$10^8$ cells | N/A | ii. Selection of Aptamers Specific to *S. pyogenes* M11

Single colonies of ten *S. pyogenes* M-types (M1, M2, M3, M4, M6, M11, M12, M28, M77, and M89) were grown overnight in separate liquid cultures. The cells were then harvested the next morning in order to decrease variability between M-types since surface molecule expression levels off in stationary phase. Aliquots containing the same number of cells from each culture were combined only once growth was complete. Cell mixtures were centrifuged at 6000×g and 4° C. for 10 minutes to remove media and to remove wash supernatants. Two separate sets of SELEX were carried out: SELEX D and SELEX E. The varying conditions of both SELEX sets are summarized in Table 7.

Both SELEX D and E were initiated with ssDNA library (1 mmol initial round for SELEX D and SELEX E). The library used in SELEX E was only the reverse strand of the PCR-amplified initial library yet the same total amount of DNA (1 μmol) was used as in SELEX D. The aptamer pools used for incubation in SELEX D and E were decreased from 1 μmol for rounds 1 through 4, to 100 pmole for rounds 5 through 8. A total of $10^9$ cells, containing an equal number of cells of each M-type ($10^8$), were used for each round of selection for both SELEX D and E. An excess of tRNA and BSA (Invitrogen) were added to the incubation buffer (20-fold molar excess of each in round 5, up to a maximum 60-fold molar excess in round 8) and 0.05% w/v BSA was added to the wash buffer in rounds 5 through 8. All washes and incubations were carried out in 1× Binding Buffer (1×BB) (50 mM Tris-HCl (pH 7.4), 5 mM KCl, 100 mM NaCl, 1 mM $MgCl_2$) at room temperature for 60 minutes. Incubation volumes for this set of selections were increased over previous sets (GAS SELEX A and B) and incubations were carried out under rotation in order to increase the likelihood of DNA and target cell contact. An initial incubation volume of 2 mL was used for round one, and this was decreased to 1 mL for round 2 and the counterselection round, 0.5 mL for rounds 4 and 5, and 0.25 mL for rounds 6 to 8. A total of 3 washes were carried out for each round of SELEX D and E until round 5 at which the number of washes was increased to 4 in order to increase the stringency of the selection conditions. Aptamers were then eluted by heating the cells in 1×PCR Buffer (Invitrogen) at 94° C. for 5 minutes followed by 10 minutes on ice. The cells then centrifuged at 6,000×g and 4° C. for 10 minutes and the supernatant retained as the heat eluted (CA) fraction. The cell pellet was then resuspended in 1×PCR buffer and retained as the cell (Cells) fraction. A total of 8 rounds of SELEX D and 8 rounds of SELEX E were completed.

Example 6

Counterselection

A counterselection step was carried out after 2 rounds of SELEX D and E against the *S. pyogenes* mixture. The purpose of the counterselection step is to remove sequences from the aptamer pools that are not specific for *S. pyogenes*. *S. bovis* liquid cultures were grown overnight in BHI broth at 37° C. and 200 rpm. Cells were harvested in the morning via centrifugation, and $10^9$ cells were resuspended in 1×BB and

TABLE 7

Summary of conditions used in GAS SELEX D and E.

| SELEX set | SELEX D | SELEX E |
|---|---|---|
| Initial starting library | Use entire IDT tube ($10^{16}$ different sequences) | Amplify library and gel purify reverse strand ($10^{14}$ different sequences) |
| Number of cells | $10^9$ Total cells<br>$10^8$ per M type | $10^9$ Total cells<br>$10^8$ per M type |
| Incubation | 2 mL volume round 1<br>1 mL volume round 2<br>0.5 mL volume rounds 4, 5<br>0.25 mL volume rounds 6, 7, 8<br>1 hour at RT | 2 mL volume round 1<br>1 mL volume round 2<br>0.5 mL volume rounds 4, 5<br>0.25 mL volume rounds 6, 7, 8<br>1 hour at RT |
| Washes | Same as incubation volume | Same as incubation volume |
| CA fraction (heat-eluted) | 500 μL 1X PCR buffer<br>94° C. for 5 minutes | 500 μL 1X PCR buffer<br>94° C. for 5 minutes |
| Cell fraction | 500 μL 1X PCR buffer | 500 μL 1X PCR buffer |
| Number of PCR cycles | Optimize after each round until 20 cycles no longer produces misamplification | Optimize after each round until 20 cycles no longer produces misamplification | incubated with 1 µmole aptamer pool 2D or 2E in 1 mL final volume at room temperature for 60 minutes. Following incubation, the cells were treated as during SELEX, and the supernatant and three wash fractions were retained. The supernatant volume was 1 mL and each wash fraction was 1 mL. Aptamers from these fractions were ethanol precipitated, resuspended in 10 mM Tris pH 8.0, pooled, and then amplified under standard conditions using a polyA Sp9 forward primer and regular reverse primer. The 80-nt reverse strand of the resultant amplicons was gel purified as described previously.

Example 7

Flow Cytometric Analysis of Aptamer Pool and Individual Aptamer Binding

A FACScan flow cytometer with PowerMac G4 workstation and CellQuest software (Flow Cytometry Facility, Faculty of Medicine and Dentistry, University of Alberta) was used to assess the binding of the aptamer pool and individual aptamer sequences to different types of cells (*S. pyogenes, Enterococcus* sp., *S. pneumoniae, S. agalactiae, E. coli* DH5a, *S. bovis*). The aptamer pools were fluorescently-labeled via PCR amplification with 5'-FAM modified reverse primers (IDT) and the polyA-Sp9 forward primer, whereas the individual aptamer sequences were purchased with the fluorescent label (5'-FAM) attached (IDT). Aptamer pools were heat denatured prior to incubation with bacterial cells. The binding assays were carried out by incubating 200 pmole of fluorescently-labeled aptamer/aptamer pool with $10^8$ cells for 45 min, as in the SELEX process. Cells were then centrifuged at 6,000×g and 4° C. for 10 minutes, washed once in 1× binding buffer, and resuspended in 1× binding buffer for flow cytometry analysis. 10,000 events were counted for each analysis; triplicate analyses of triplicate incubations were carried out.

In cases where mixtures of cells were used, an equal number of each cell type was combined to a total of $10^8$ cells for screenings and $10^9$ cells for binding curves. Forward scatter, side scatter, and fluorescence intensity (FL1-H) were measured, and gated fluorescence intensity above background (cells with no aptamers added) was quantified. The average percent gated fluorescence of the cells bound to the library was subtracted from the values measured for each aptamer pool. Fluorescently-labeled ssDNA library was used as a control for non-specific binding in each experiment. Binding curves were run to estimate $K_d$s by varying aptamer concentrations (0-150 nM incubation) with a fixed number of cells ($10^9$). GraphPad Prism™ 5.0 software was used to predict $K_d$ values. All cultures used for flow cytometric screening were harvested in stationary phase in order to minimize differences in cell surface molecule expression.

Example 8

Cloning, Sequencing and Structural Analysis of Aptamers i. Selection of Aptamers Specific to a Plurality of Strains of *S. pyogenes*

The highest affinity aptamer pools measured via flow cytometry were chosen for sequencing analysis: pools 15A, 13B, and 20A.

ii. Selection of Aptamers Specific to *S. pyogenes* M11

The highest affinity aptamer pools measured via flow cytometry were chosen for sequencing analysis: pools 8D and 8E.

For both i and ii above, aptamer pools were cloned using a TOPO TA Cloning Kit for Sequencing (Invitrogen), transformed into *E. coli* DH5α-T1$^R$ cells (Invitrogen), and colonies containing the vector were selected via overnight incubation at 37° C. on LB plates containing 50 µg/mL kanamycin. From each aptamer pool, 20 colonies (first study) or 40 colonies (second study) were chosen for screening. The plasmid DNA was purified (Qiaex II gel extraction kit; Qiagen, Mississauga, ON) and analyzed for the presence of an 80 bp insert via digestion with 1 U of EcoR1 at 37° C. for 30 minutes, followed by 7.5% native PAGE. A total of 60 inserts (first study) or 80 inserts (second study) were then sequenced (Applied Genomics Center, Department of Medical Genetics, University of Alberta), yielding 57 useable sequences (i above) or 51 useable sequences (ii above). The secondary structure of each sequence both with and without primers was predicted using Oligoanalyzer™ 3.0 (IDT), with input conditions of room temperature (21° C.) and 1 mM MgCl$_2$. The most likely sequence was taken as that with the lowest predicted free energy of formation ($\Delta G$) (kcal/mole).

Example 9

Sequences with Repetitive Fragments

Sequences repeated within and between aptamer pools 15A and 20A as listed in Table 1 (SEQ ID NOS: 1-3); screened aptamer sequences with and without primers as listed in Table 2 (SEQ ID NOS: 4-15); and screened SELEX D and E aptamer pool sequences as listed in Table 4 (SEQ ID NOS: 16, 18, 22, 23, 25, 26, and 29-32) were compared. Table 8 highlights the different fragments which are repeated among these particular sequences.

TABLE 8

Summary of repetitive fragments within various sequences

| Name | Sequence |
|---|---|
| D-Cells 9 | 5'-GGGGAGGAGAAAAAGAGGACCAGAGTAACGATTCGTGGGG-3' (SEQ ID NO: 22) |
| D-Cells 9P | 5'-<u>TTCACGGTAGCACGCATAGG</u>GGGGAGGAGAAAAAGAGG ACCAGAGTAACGATTCGTGGGG<u>CATCTGACCTCTGTGCTGCT</u>-3' (SEQ ID NO: 23) |
| D-Cells 20P | 5'-<u>TTCACGGTAGCACGCATAGG</u>GGGGAGGAGAAAATAGAGGA CCAGAGTAACGATTCGTGGGG<u>CATCTGACCTCTGTGCTGCT</u>-3' (SEQ ID NO: 25) |
| E-CA 20 | 5'-CACACACGGAACCCCGACAACATACATACGGTGAGGGTGG-3' (SEQ ID NO: 29) |
| E-CA 20P | 5'-<u>TTCACGGTAGCACGCATAGG</u>CACACACGGAACCCCGACAAC ATACATACGGTGAGGGTGG<u>CATCTGACCTCTGTGCTGCT</u>-3' (SEQ ID NO: 30) |
| E-Cells 1 | 5'-GGGGAGGAGAAAAGAGGACCAGAGTAACGATTCGTGGGG-3' (SEQ ID NO: 31) |
| E-Cells 1P | 5'-<u>TTCACGGTAGCACGCATAGG</u>GGGGAGGAGAAAAGAGGACCA GAGTAACGATTCGTGGGG<u>CATCTGACCTCTGTGCTGCT</u>-3' (SEQ ID NO: 32) |

TABLE 8-continued

Summary of repetitive fragments within various sequences

| Name | Sequence |
|---|---|
| E CA 4 | 5'-GGCACCAAGCAAAAATCGTAATGTTGGTGGTACACTTCGG-3' (SEQ ID NO: 26) |
| D CA cells 6 | 5'-<u>GACGGGCGAGGAGGGGACCTCAAGTGGGTTCGGTG</u>-3' (SEQ ID NO: 16) |
| D CA 17 | 5'-<u>GACGGTTCTGAGGGAGGGGACCTCAAGTGGGTTCGGTG</u>-3' (SEQ ID NO: 18) |
| 15A 2 | 5'-GACACCAAGCTAAGATCGTAATGTTGGTGGTACACTTCGG-3' (SEQ ID NO: 1) |
| 15A 8 | 5'-GGT*CCAAGG*TTATATCGAAGTGGCCTGCAGCCTGCAACGG-3' (SEQ ID NO: 2) |
| 15A 10 | 5'-CCCACCCCCGTCACTTCCTTCTTCCCAGTGTCTCCACGTC-3' (SEQ ID NO: 3) |
| 20A 1 | 5'-CAGAACGCACCCGCACACCTCCATCACTCGCA*TGCACCCC*-3' (SEQ ID NO: 4) |
| 20A 1P | 5'-<u>TTC ACG GTA GCA CGC ATA GG</u> CAGAACGCACCCGCACACCTCCATCACTCG CA*TGCACCCC* <u>CAT CTG ACC TCT GTG CTG CT</u>-3' (SEQ ID NO: 5) |
| 20A 8 | 5'-CCCCACGAATCGTTACTCTGGTCCTCTATTTC*TCCTCCCC*-3' (SEQ ID NO: 6) |
| 20A 8P | 5'-<u>AGC AGC ACA GAG GTC AGA TG</u> CCCCACGAATCGTTACTCTGGTCCTCTATTTCT *CCTCCCC* <u>CCT ATG CGT GCT ACC GTG AA</u>-3' (SEQ ID NO: 7) |
| 20A 9 | 5'-CACACGCTGAAGAAAC*TGAGG*TCGTAGGTTTTCTTCGGG-3' (SEQ ID NO: 8) |
| 20A 9P | 5'-<u>AGC AGC ACA GAG GTC AGA TG</u> CACACGCTGAAGAAAC*TGAGG*TCGTAGGTTTT CTTCGGG <u>CCT ATG CGT GCT ACC GTG AA</u>-3' (SEQ ID NO: 9) |
| 20A 12P | 5'-<u>TTC ACG GTA GCA CGC ATA GG</u> GCCCGACACTCGTCCACCCGATACCTCT CATGTGTCCC <u>CAT CTG ACC TCT GTG CTG CT</u>-3' (SEQ ID NO: 10) |
| 20A 14P | 5'-<u>AGC AGC ACA GAG GTC AGA TG</u> GGCATGGGAA*GAGAAAG*CGGGATAACTTCGTT ACCGGGC <u>CCT ATG CGT GCT ACC GTG AA</u>-3' (SEQ ID NO: 11) |
| 20A24 | 5'-GGGGGAAGACAC*AGAGAAAG*GCCGGGGTGAAGTG*TAGAGG*-3' (SEQ ID NO: 12) |
| 20A24P | 5'-<u>AGC AGC ACA GAG GTC AGA TG</u> GGGGGAAGACAC*AGAGAAAG*GCCGGGGTGAAGT G*TAGAGG* <u>CCT ATG CGT GCT ACC GTG AA</u>-3' (SEQ ID NO: 13) |
| 15A3 | 5'-GACAGCAAGCCCAAGCTGGGTGTGCAAGG*TGAGG*AGTGGG-3' (SEQ ID NO: 14) |
| 15A 3P | 5'-<u>TTC ACG GTA GCA CGC ATA GG</u> *GACAGCAAGCCCAAGCT*GGGTGTGCAAGGT *GAGGA*GTGGG <u>CAT CTG ACC TCT GTG CTG CT</u>-3' (SEQ ID NO: 15) |

REFERENCES

The following references are incorporated herein by reference (where permitted) as if reproduced in their entirety. All references are indicative of the level of skill of those skilled in the art to which this invention pertains.

Armengol C E, Schlager T A, Hendley J O. Sensitivity of a rapid antigen detection test for group A streptococci in a private pediatric office setting: Answering the red book's request for validation. Pediatrics. 2004 April; 113 (4):924-6.

Ausubel, F. M., Brent, R., Kingston, R. E., Moore, D. D., Deidman, J. G. and Tatham, A. S. (1995) Current Protocols in Molecular Biology. New York.

Beachey E H, Seyer J M, Dale J B, Simpson W A, Kang A H. Type-specific protective immunity evoked by synthetic peptide of Streptococcus pyogenes M protein. Nature 1981 Jul. 30; 292(5822):457-9.

Beall B, Facklam R, Thompson T. Sequencing emm-specific PCR products for routing and accurate typing of group A streptococci. J. Clin. Microbiol. 1996 April; 34(4):953-8.

Beall B W, Gertz R E, Hulkower R L, Whitney C G, Moore M R, Brueggemann A B. Shifting genetic structure of invasive serotype 19A pneumococci in the United States. J Infect Dis, 2011 Mar. 16.

Berezovski M, Drabovich A, Krylova S M, Musheev M, Okhonin V, Petrov A, Krylov S N. Nonequilibrium capillary electrophoresis of equilibrium mixtures: A universal tool for development of aptamers. J Am Chem. Soc. 2005 Mar. 9; 127(9):3165-71.

Bruno J G, Kiel J L. In vitro selection of DNA aptamers to anthrax spores with electrochemiluminescence detection. Biosens Bioelectron. 1999 May 31; 14(5):457-64.

Bruno J G, Kiel J L. Use of magnetic beads in selection and detection of biotoxin aptamers by electrochemiluminescence and enzymatic methods. BioTechniques. 2002 January; 32(1):178, 80, 182-3.

Bruno J G, Carrillo M P, Phillips T, Andrews C J. A novel screening method for competitive FRET-aptamers applied to E. coli assay development. J. Fluoresc. 2010 May 5.

Cao X, Li S, Chen L, Ding H, Xu H, Huang Y, Li J, Liu N, Cao W, Zhu Y, Shen B, Shao N. Combining use of a panel of ssDNA aptamers in the detection of staphylococcus aureus. Nucleic Acids Res, 2009 August; 37(14):4621-8.

CDC 2007. Group A Streptococcal Disease. URL: http://www.cdc.gov/ncidod/dbmd/diseaseinfo/groupastreptococcal_g.htm Chen F, Zhou J, Luo F, Mohammed A B, Zhang X L. Aptamer from whole-bacterium SELEX as new therapeutic reagent against virulent mycobacterium tuberculosis. Biochem Biophys Res Commun. 2007 Jun. 8; 357(3):743-8.

Cho E J, Collett J R, Szafranska A E, Ellington A D. Optimization of aptamer microarray technology for multiple protein targets. Anal Chim Acta. 2006 Mar. 30; 564(1):82-90. Epub 2006 Jan. 23.

Drabovich A, Berezovski M, Krylov S N. Selection of smart aptamers by equilibrium capillary electrophoresis of equilibrium mixtures (ECEEM). J Am Chem. Soc. 2005 Aug. 17; 127(32):11224-5.

Dwivedi H P, Smiley R D, Jaykus L A. Selection and characterization of DNA aptamers with binding selectivity to campylobacter jejuni using whole-cell SELEX. Appl Microbiol Biotechnol. 2010 August; 87(6):2323-34.

Ellington A D, Szostak J W. In vitro selection of RNA molecules that bind specific ligands. Nature. 1990 Aug. 30; 346(6287):818-22.

Facklam R R, Moody M D. Production of streptococcal M-typing antisera. I. Antigenic response in different breeds of rabbits. Appl. Microbiol. 1968 December; 16(12):1822-5.

Facklam R, Beall B, Efstratiou A, Fischetti V, Johnson D, Kaplan E, Kriz P, Lovgren M, Martin D, Schwartz B, Totolian A, Bessen D, Hollingshead S, Rubin F, Scott J, Tyrrell G. emm typing and validation of provisional M types for group A streptococci. Emerg. Infect. Dis. 1999 March-April; 5(2):247-53.

Fan M, McBurnett S R, Andrews C J, Allman A M, Bruno J G, Kiel J L. Aptamer selection express: A novel method for rapid single-step selection and sensing of aptamers. J Biomol Tech. 2008 December; 19(5):311-9.

Fischetti V A. Streptococcal M protein. Sci. Am. 1991 June; 264(6):58-65.

Fischetti Va. Streptococcal M protein: molecular design and biological behavior. Clin Microbiol Rev. 1989 July; 2(3): 285-314.

Gardiner D, Hartas J, Currie B, Mathews J D, Kemp D J, Sriprakash K S. Vir typing: a long-PCR typing method for group A streptococci. PCR Methods Appl. 1995 April; 4(5):288-93.

Hamula C L, Zhang H, Guan L L, Li X F, Le X C. Selection of aptamers against live bacterial cells. Anal Chem. 2008 Oct. 15; 80(20):7812-9.

Ikanovic M, Rudzinski W E, Bruno J G, Allman A, Carrillo M P, Dwarakanath S, Bhandigadi S, Rao P, Kiel J L, Andrews C J. Fluorescence assay based on aptamer-quantum dot binding to bacillus thuringiensis spores. J. Fluoresc. 2007 March; 17(2):193-9.

Jensen K B, Atkinson B L, Willis M C, Koch T H, Gold L. Using in vitro selection to direct the covalent attachment of human immunodeficiency virus type 1 rev protein to high-affinity RNA ligands. Proc Natl Acad Sci USA. 1995 Dec. 19; 92(26):12220-4.

Jones, K F and Fischetti V A. The importance of the location of antibody binding on the M6 protein for opsonization and phagocytosis of group A M6 streptococci. J. Exp. Med. 1988 Mar. 1; 167(3):1114-23.

Kaufhold A, Podbielski A, Baumgarten G, Blokpoel M, Top J, Schouls L. Rapid typing of group A streptococci by the use of DNA amplification and non-radioactive allele-specific oligonucleotide probes. FEMS Microbiol Lett. 1994 Jun. 1; 119(1-2):19-25.

Kirby R, Cho E J, Gehrke B, Bayer T, Park Y S, Neikirk D P, McDevitt J T, Ellington A D. Aptamer-based sensor arrays for the detection and quantitation of proteins. Anal Chem. 2004 Jul. 15; 76(14):4066-75.

Kolter R, Siegele D A, Tormo A. The stationary phase of the bacterial life cycle. Annu Rev Microbiol. 1993; 47:855-74.

Lancefield, R C. A serological differentiation of human and other groups of hemolytic streptococci. J. Exp. Med. 1933 Mar. 31; 5(4):571-95.

Lancefield, R C. Current knowledge of type-specific M antigens of group A streptococci. J. Immunol. 1962 September; 89:307-13.

Leung A K, Newman R, Kumar A, Davies H D. Rapid antigen detection testing in diagnosing group A beta-hemolytic streptococcal pharyngitis. Expert Rev Mol. Diagn. 2006 September; 6(5):761-6.

Mendonsa S D, Bowser M T. In vitro selection of high-affinity DNA ligands for human IgE using capillary electrophoresis. Anal Chem. 2004 Sep. 15; 76(18):5387-92, Mendonsa S D, Bowser M T. In vitro selection of aptamers with affinity for neuropeptide Y using capillary electrophoresis. J Am Chem. Soc. 2005 Jul. 6; 127(26):9382-3.

Morris K N, Jensen K B, Julin C M, Weil M, Gold L. High affinity ligands from in vitro selection: Complex targets. Proc Natl Acad Sci USA. 1998 Mar. 17; 95(6):2902-7.

Neal S, Beall B, Ekelund K, Henriques-Normark B, Jasir A, Johnson D, Kaplan E, Lovgren M, Reinert R R; Strep-EURO Study Group; International Streptococcus Reference Laboratories, Efstratiou A. International quality assurance study for characterization of Streptococcus pyogenes. J. Clin. Microbiol. 2007 April; 45(4):1175-9.

Saunders N A, Hallas G, Gaworzewska E T, Metherell L, Efstratiou A, Hookey J Y, George R C. PCR-enzyme-linked immunosorbent assay and sequencing as an alternative to serology for M-antigen typing of Streptococcus pyogenes. J Clin Microbiol. 1997 October; 35(10):2689-91.

Sefah K, Shangguan D, Xiong X, O'Donoghue M B, Tan W. Development of DNA aptamers using cell-SELEX. Nat Protoc. 2010; 5(6):1169-85.

Shangguan D, Cao Z C, Li Y, Tan W. Aptamers evolved from cultured cancer cells reveal molecular differences of cancer cells in patient samples. Clin Chem. 2007 June; 53(6): 1153-5.

Sharkawy A, Low D E, Saginur R, Gregson D, Schwartz B, Jessamine P, Green K, McGeer A; Ontario Group A Streptococcal Study Group. Severe group A streptococcal soft-tissue infections in Ontario: 1922-1996. Clin Infect Dis. 2002 Feb. 15; 34(4):454-60. Epub 2002 Jan. 7.

Stoltenburg R, Reinemann C, Strehlitz B. SELEX—a (r) evolutionary method to generate high-affinity nucleic acid ligands. Biomol Eng. 2007 October; 24(4):381-403. Epub 2007 Jun. 16.

Tang Z, Shangguan D, Wang K, Shi H, Sefah K, Mallikratchy P, et al. Selection of aptamers for molecular recognition and characterization of cancer cells. Anal Chem. 2007 Jul. 1; 79(13):4900-7.

Tang Z, Parekh P, Turner P, Moyer R W, Tan W. Generating aptamers for recognition of virus-infected cells. Clin Chem. 2009 April; 55(4):813-22.

Tuerk C, Gold L. Systematic evolution of ligands by exponential enrichment: RNA ligands to bacteriophage T4 DNA polymerase. Science. 1990 Aug. 3; 249(4968):505-10.

Tyrrell G J, Lovgren M, Forwick B, Hoe N P, Musser J M, Talbot J A. M types of group a streptococcal isolates submitted to the national centre for streptococcus (Canada) from 1993 to 1999. J Clin Microbiol. 2002 December; 40(12):4466-71.

Vlaminckx B J, Mascini E M, Schellekens J F. Invasive Lancefield group A streptococcal infections in the Netherlands. Ned Tijdschr Geneeskd. 2007 Jul. 28; 151(30):1669-73.

Whatmore A M, Kapur V, Sullivan D J, Musser J M, Kehoe M A. Non-congruent relationships between variation in emm gene sequences and the population genetic structure of group A streptococci. Mol. Microbiol, 1994 November; 14(4): 619-31.

White R, Rusconi C, Scardino E, Wolberg A, Lawson J, Hoffman M, Sullenger B. Generation of species cross-reactive aptamers using "toggle" SELEX. Mol. Ther. 2001 December; 4(6):567-73.

What is claimed is:

1. A method of screening a subject for *Streptococcus pyogenes* comprising the steps of:
   a) obtaining a body sample from the subject;
   b) contacting the sample or a bacterial culture of the sample with an aptamer or a panel of aptamers specific to *S. pyogenes*, wherein the aptamer or the panel of aptamers comprises the nucleic acid sequence as set forth in any one of SEQ ID NOS: 1-32, or a nucleic acid sequence having at least 80%, at least 85%, at least 90%, at least 95%, at least 96%, at least 97%, at least 98%, or at least 99% sequence identity therewith over the entire length of said any one of SEQ ID NOS: 1-32; and
   c) detecting the presence or absence of *S. pyogenes* in the sample or the bacterial culture, wherein binding of the aptamer or the panel of aptamers is indicative of the presence of *S. pyogenes*.

2. The method of claim 1, wherein the sample is selected from urine, blood, plasma, serum, saliva, a throat swab, a skin swab, wound aspirate, ocular fluid, spinal fluid, or perspiration.

3. The method of claim 1, wherein the aptamer is specific to a plurality of M-type strains of *S. pyogenes*.

4. The method of claim 3, wherein the M-type strains comprise M1, M2, M3, M4, M5, M6, M11, M12, M28, M41, M49, M59, M75, M77, M82, M83, M89, M91, M92, and M114.

5. The method of claim 3, wherein the aptamer comprises the nucleic acid sequence as set forth in SEQ ID NO: 9, SEQ ID NO: 13 or SEQ ID NO: 15.

6. The method of claim 1, wherein the aptamer is specific to *S. pyogenes* M11.

7. The method of claim 6, wherein the aptamer comprises the nucleic acid sequence as set forth in any one of SEQ ID NOS: 16-32, or a nucleic acid sequence having at least 80%, at least 85%, at least 90%, at least 95%, at least 96%, at least 97%, at least 98%, or at least 99% sequence identity therewith over the entire length of said any one of SEQ ID NOS: 16-32.

8. The method of claim 6, wherein the aptamer comprises the nucleic acid sequence as set forth in SEQ ID NO: 29, SEQ ID NO: 30 or SEQ ID NO: 32.

9. The method of claim 1, wherein the aptamer has a binding dissociation constant less than or equal to 100 nM.

10. The method of claim 9, wherein the aptamer has a binding dissociation constant less than or equal to 10 nM.

11. The method of claim 1, wherein the aptamer comprises single or double-stranded DNA.

12. The method of claim 1, wherein the aptamer comprises single or double-stranded RNA.

13. The method of claim 1, wherein before step (b), the aptamers are selected using SELEX comprising a mixture of whole bacterial cells.

14. The method of claim 13, wherein the aptamer is labeled with a fluorescent compound.

15. A method of screening a subject for Group B *Streptococcus* comprising the steps of:
    a) obtaining a body sample from the subject;
    b) contacting the sample or a bacterial culture of the sample with an aptamer comprising the nucleic acid sequence as set forth in SEQ ID NO: 6 or SEQ ID NO: 21;
    c) detecting the presence or absence of Group B *Streptococcus* in the sample or the bacterial culture, wherein binding of the aptamer is indicative of the presence of Group B *Streptococcus*.

16. An isolated nucleic acid having the nucleic acid sequence as set forth in any one of SEQ ID NOS: 1-32, or having at least 80%, at least 85%, at least 90%, at least 95%, at least 96%, at least 97%, at least 98%, or at least 99% sequence identity therewith over the entire length of said any one of SEQ ID NOS: 1-32.

17. A kit for detecting the presence of *S. pyogenes* comprising an aptamer or a panel of aptamers wherein the aptamer or the panel of aptamers comprises the nucleic acid sequence as set forth in any one of SEQ ID NOS: 1-32, or a nucleic acid sequence having at least 80%, at least 85%, at least 90%, at least 95%, at least 96%, at least 97%, at least 98%, or at least 99% sequence identity therewith over the entire length of said any one of SEQ ID NOS: 1-32, reagents for detecting the binding of the aptamer or panel of aptamers to *S. pyogenes*, and one or more supports.

\* \* \* \* \*

UNITED STATES PATENT AND TRADEMARK OFFICE
CERTIFICATE OF CORRECTION

PATENT NO. : 8,507,203 B2
APPLICATION NO. : 13/433553
DATED : August 13, 2013
INVENTOR(S) : X. Chris Le, Camille Hamula and Xing-Fang Li It is certified that error appears in the above-identified patent and that said Letters Patent is hereby corrected as shown below:

| On the Title Page | Error Correction Should Read |
|---|---|
| Item (75) Inventors | Xing-Fang Li, Edmonton (CA) |
| Item (73) Assignee | The Governors of the University of Alberta, Edmonton, Alberta (CA) |

Signed and Sealed this
Thirty-first Day of December, 2013

Margaret A. Focarino
*Commissioner for Patents of the United States Patent and Trademark Office*

SEQUENCE LISTING

<160> NUMBER OF SEQ ID NOS: 37

<210> SEQ ID NO 1
<211> LENGTH: 40
<212> TYPE: DNA
<213> ORGANISM: Artificial Sequence
<220> FEATURE:
<223> OTHER INFORMATION: Sequence repeated within aptamer pool 15A; occurrence in 15A2 and 15A15

<400> SEQUENCE: 1
gacaccaagc taagatcgta atgttggtgg tacacttcgg                                40

<210> SEQ ID NO 2
<211> LENGTH: 40
<212> TYPE: DNA
<213> ORGANISM: Artificial Sequence
<220> FEATURE:
<223> OTHER INFORMATION: Sequence repeated within aptamer pool 15A; occurrence in 15A 8, 15A16, 15A17

<400> SEQUENCE: 2
ggtccaaggt tatatcgaag tggcctgcag cctgcaacgg                                40

<210> SEQ ID NO 3
<211> LENGTH: 40
<212> TYPE: DNA
<213> ORGANISM: Artificial Sequence
<220> FEATURE:
<223> OTHER INFORMATION: Sequence repeated within and between aptamer pools 15A and 20A; occurrence in 15A10, 20A6, 20A15, and 20A17

<400> SEQUENCE: 3 cccaccccg tcacttcctt cttcccggtg tctccacgtc                                 40

<210> SEQ ID NO 4
<211> LENGTH: 40
<212> TYPE: DNA
<213> ORGANISM: Artificial Sequence
<220> FEATURE:
<223> OTHER INFORMATION: 20A1; FAM-labelled

<400> SEQUENCE: 4
cagaacgcac ccgcacacct ccatcactcg catgcacccc                                40

<210> SEQ ID NO 5
<211> LENGTH: 80
<212> TYPE: DNA
<213> ORGANISM: Artificial Sequence
<220> FEATURE:
<223> OTHER INFORMATION: 20A1P; FAM-labelled

<400> SEQUENCE: 5
ttcacggtag cacgcatagg cagaacgcac ccgcacacct ccatcactcg catgcacccc          60
catctgacct ctgtgctgct                                                      80

<210> SEQ ID NO 6
<211> LENGTH: 40
<212> TYPE: DNA
<213> ORGANISM: Artificial Sequence
<220> FEATURE:
<223> OTHER INFORMATION: 20A8; FAM-labelled

<400> SEQUENCE: 6
ccccacgaat cgttactctg gtcctctatt tctcctcccc                                40

```
<210> SEQ ID NO 7
<211> LENGTH: 80
<212> TYPE: DNA
<213> ORGANISM: Artificial Sequence
<220> FEATURE:
<223> OTHER INFORMATION: 20A8P; FAM-labelled

<400> SEQUENCE: 7
agcagcacag aggtcagatg ccccacgaat cgttactctg gtcctctatt tctcctcccc    60
cctatgcgtg ctaccgtgaa                                                80

<210> SEQ ID NO 8
<211> LENGTH: 39
<212> TYPE: DNA
<213> ORGANISM: Artificial Sequence
<220> FEATURE:
<223> OTHER INFORMATION: 20A9; FAM-labelled

<400> SEQUENCE: 8
cacacgctga agaaactgag gtcgtaggtt ttcttcggg                            39

<210> SEQ ID NO 9
<211> LENGTH: 79
<212> TYPE: DNA
<213> ORGANISM: Artificial Sequence
<220> FEATURE:
<223> OTHER INFORMATION: 20A9P; FAM-labelled

<400> SEQUENCE: 9
agcagcacag aggtcagatg cacacgctga agaaactgag gtcgtaggtt ttcttcgggc    60
ctatgcgtgc taccgtgaa                                                 79

<210> SEQ ID NO 10
<211> LENGTH: 78
<212> TYPE: DNA
<213> ORGANISM: Artificial Sequence
<220> FEATURE:
<223> OTHER INFORMATION: 20A12P; FAM-labelled

<400> SEQUENCE: 10
ttcacggtag cacgcatagg gcccgacact cgtccacccg atacctctca tgtgtcccca    60
tctgacctct gtgctgct                                                  78

<210> SEQ ID NO 11
<211> LENGTH: 80
<212> TYPE: DNA
<213> ORGANISM: Artificial Sequence
<220> FEATURE:
<223> OTHER INFORMATION: 20A14P; FAM-labelled

<400> SEQUENCE: 11
agcagcacag aggtcagatg ggcatgggga agagaaagcg ggataacttc gttaccgggc    60
cctatgcgtg ctaccgtgaa                                                80

<210> SEQ ID NO 12
<211> LENGTH: 40
<212> TYPE: DNA
<213> ORGANISM: Artificial Sequence
<220> FEATURE:
<223> OTHER INFORMATION: 20A24; FAM-labelled

<400> SEQUENCE: 12
gggggaagac acagagaaag gccggggtga agtgtagagg                          40
```

<210> SEQ ID NO 13
<211> LENGTH: 80
<212> TYPE: DNA
<213> ORGANISM: Artificial Sequence
<220> FEATURE:
<223> OTHER INFORMATION: 20A24P; FAM-labelled

<400> SEQUENCE: 13
agcagcacag aggtcagatg gggggaagac acagagaaag gccggggtga agtgtagagg    60
cctatgcgtg ctaccgtgaa                                                80

<210> SEQ ID NO 14
<211> LENGTH: 40
<212> TYPE: DNA
<213> ORGANISM: Artificial Sequence
<220> FEATURE:
<223> OTHER INFORMATION: 15A3; FAM-labelled

<400> SEQUENCE: 14
gacagcaagc ccaagctggg tgtgcaaggt gaggagtggg                          40

<210> SEQ ID NO 15
<211> LENGTH: 80
<212> TYPE: DNA
<213> ORGANISM: Artificial Sequence
<220> FEATURE:
<223> OTHER INFORMATION: 15A3P; FAM-labelled

<400> SEQUENCE: 15
ttcacggtag cacgcatagg gacagcaagc ccaagctggg tgtgcaaggt gaggagtggg    60
catctgacct ctgtgctgct                                                80

<210> SEQ ID NO 16
<211> LENGTH: 35
<212> TYPE: DNA
<213> ORGANISM: Artificial Sequence
<220> FEATURE:
<223> OTHER INFORMATION: aptamer pool sequence; D CA CELLS 6

<400> SEQUENCE: 16
gacgggcgag gaggggacct caagtgggtt cggtg                               35

<210> SEQ ID NO 17
<211> LENGTH: 74
<212> TYPE: DNA
<213> ORGANISM: Artificial Sequence
<220> FEATURE:
<223> OTHER INFORMATION: aptamer pool sequence; D CA CELLS 6P

<400> SEQUENCE: 17
agcagcacag aggtcagatg gacgggcgag gaggggacct caagtgggtt cggtgcctat    60
gctgctaccg tgaa                                                      74

<210> SEQ ID NO 18
<211> LENGTH: 38
<212> TYPE: DNA
<213> ORGANISM: Artificial Sequence
<220> FEATURE:
<223> OTHER INFORMATION: aptamer pool sequence; D CA 17; FAM-labelled

<400> SEQUENCE: 18
gacggttctg agggagggga cctcaagtgg gttcggtg                            38

```
<210> SEQ ID NO 19
<211> LENGTH: 78
<212> TYPE: DNA
<213> ORGANISM: Artificial Sequence
<220> FEATURE:
<223> OTHER INFORMATION: aptamer pool sequence; D CA 17P

<400> SEQUENCE: 19
agcagcacag aggtcagatg gacggttctg agggagggga cctcaagtgg gttcggtgcc    60
tatgcgtgct accgtgaa                                                  78

<210> SEQ ID NO 20
<211> LENGTH: 40
<212> TYPE: DNA
<213> ORGANISM: Artificial Sequence
<220> FEATURE:
<223> OTHER INFORMATION: aptamer pool sequence; D CELLS 1

<400> SEQUENCE: 20
ccccacgaat cggtactctg gtcctctatt tctcctcccc                          40

<210> SEQ ID NO 21
<211> LENGTH: 80
<212> TYPE: DNA
<213> ORGANISM: Artificial Sequence
<220> FEATURE:
<223> OTHER INFORMATION: aptamer pool sequence; D CELLS 1P

<400> SEQUENCE: 21
agcagcacag aggtcagatg ccccacgaat cggtactctg gtcctctatt tctcctcccc    60
cctatgcgtg ctaccgtgaa                                                80

<210> SEQ ID NO 22
<211> LENGTH: 40
<212> TYPE: DNA
<213> ORGANISM: Artificial Sequence
<220> FEATURE:
<223> OTHER INFORMATION: aptamer pool sequence; D CELLS 9; FAM-labelled

<400> SEQUENCE: 22
ggggaggaga aaaagaggac cagagtaacg attcgtgggg                          40

<210> SEQ ID NO 23
<211> LENGTH: 80
<212> TYPE: DNA
<213> ORGANISM: Artificial Sequence
<220> FEATURE:
<223> OTHER INFORMATION: aptamer pool sequence; D CELLS 9P

<400> SEQUENCE: 23
ttcacggtag cacgcatagg ggggaggaga aaaagaggac cagagtaacg attcgtgggg    60
catctgacct ctgtgctgct                                                80

<210> SEQ ID NO 24
<211> LENGTH: 40
<212> TYPE: DNA
<213> ORGANISM: Artificial Sequence
<220> FEATURE:
<223> OTHER INFORMATION: aptamer pool sequence; D CELLS 20

<400> SEQUENCE: 24
ggggaggaga aatagaggac cagagtaacg attcgtgggg                          40

<210> SEQ ID NO 25
<211> LENGTH: 80
```

```
<212> TYPE: DNA
<213> ORGANISM: Artificial Sequence
<220> FEATURE:
<223> OTHER INFORMATION: aptamer pool sequence; D CELLS 20P

<400> SEQUENCE: 25
ttcacggtag cacgcatagg ggggaggaga aatagaggac cagagtaacg attcgtgggg      60
catctgacct ctgtgctgct                                                 80

<210> SEQ ID NO 26
<211> LENGTH: 40
<212> TYPE: DNA
<213> ORGANISM: Artificial Sequence
<220> FEATURE:
<223> OTHER INFORMATION: aptamer pool sequence; E CA 4

<400> SEQUENCE: 26
ggcaccaagc aaaaatcgta atgttggtgg tacacttcgg                            40

<210> SEQ ID NO 27
<211> LENGTH: 80
<212> TYPE: DNA
<213> ORGANISM: Artificial Sequence
<220> FEATURE:
<223> OTHER INFORMATION: aptamer pool sequence; E CA 4P

<400> SEQUENCE: 27
ttcacggtag cacgcatagg ggcaccaagc aaaaatcgta atgttggtgg tacacttcgg      60
catctgacct ctgtgctgct                                                 80

<210> SEQ ID NO 28
<211> LENGTH: 79
<212> TYPE: DNA
<213> ORGANISM: Artificial Sequence
<220> FEATURE:
<223> OTHER INFORMATION: aptamer pool sequence; E CA 9P

<400> SEQUENCE: 28
agcagcacag aggtcagatg cctcacgaac ggtactctgg tcctctattt ctcctccccc      60
ctatgcgtgc taccgtgaa                                                  79

<210> SEQ ID NO 29
<211> LENGTH: 40
<212> TYPE: DNA
<213> ORGANISM: Artificial Sequence
<220> FEATURE:
<223> OTHER INFORMATION: aptamer pool sequence; E CA 20

<400> SEQUENCE: 29
cacacacgga accccgacaa catacatacg gtgagggtgg                            40

<210> SEQ ID NO 30
<211> LENGTH: 80
<212> TYPE: DNA
<213> ORGANISM: Artificial Sequence
<220> FEATURE:
<223> OTHER INFORMATION: aptamer pool sequence; E CA 20P

<400> SEQUENCE: 30
ttcacggtag cacgcatagg cacacacgga accccgacaa catacatacg gtgagggtgg      60
catctgacct ctgtgctgct                                                 80

<210> SEQ ID NO 31
<211> LENGTH: 39
```

```
<212> TYPE: DNA
<213> ORGANISM: Artificial Sequence
<220> FEATURE:
<223> OTHER INFORMATION: aptamer pool sequence; E CELLS 1

<400> SEQUENCE: 31
ggggaggaga aaagaggacc agagtaacga ttcgtgggg                                39

<210> SEQ ID NO 32
<211> LENGTH: 79
<212> TYPE: DNA
<213> ORGANISM: Artificial Sequence
<220> FEATURE:
<223> OTHER INFORMATION: aptamer pool sequence; E CELLS 1P

<400> SEQUENCE: 32
ttcacggtag cacgcatagg ggggaggaga aaagaggacc agagtaacga ttcgtggggc         60
atctgacctc tgtgctgct                                                     79

<210> SEQ ID NO 33
<211> LENGTH: 20
<212> TYPE: DNA
<213> ORGANISM: Artificial Sequence
<220> FEATURE:
<223> OTHER INFORMATION: forward primer

<400> SEQUENCE: 33
agcagcacag aggtcagatg                                                    20

<210> SEQ ID NO 34
<211> LENGTH: 20
<212> TYPE: DNA
<213> ORGANISM: Artificial Sequence
<220> FEATURE:
<223> OTHER INFORMATION: reverse primer

<400> SEQUENCE: 34
ttcacggtag cacgcatagg                                                    20

<210> SEQ ID NO 35
<211> LENGTH: 20
<212> TYPE: DNA
<213> ORGANISM: Artificial Sequence
<220> FEATURE:
<223> OTHER INFORMATION: forward primer; contains a 5' polyA overlap of
      20 adenine residues joined to the remaining primer sequence via a
      triethylene glycol spacer (IDT Spacer 9)

<400> SEQUENCE: 35
agcagcacag aggtcagatg                                                    20

<210> SEQ ID NO 36
<211> LENGTH: 20
<212> TYPE: DNA
<213> ORGANISM: Artificial Sequence
<220> FEATURE:
<223> OTHER INFORMATION: forward primer

<400> SEQUENCE: 36
agcagcacag aggtcagatg                                                    20

<210> SEQ ID NO 37
<211> LENGTH: 20
<212> TYPE: DNA
<213> ORGANISM: Artificial Sequence
<220> FEATURE:
<223> OTHER INFORMATION: reverse primer
```

```
<400> SEQUENCE: 37
ttcacggtag cacgcatagg                                              20
```